United States Patent
Holland et al.

(10) Patent No.: US 9,512,064 B2
(45) Date of Patent: Dec. 6, 2016

(54) TRANILAST COMPOSITIONS AND COCRYSTALS

(71) Applicant: NUFORMIX LIMITED, Cambridge, Cambridgeshire (GB)

(72) Inventors: Joanne Holland, Cambridge (GB); Christopher Frampton, Stowmarket (GB)

(73) Assignee: NUFORMIX LIMITED (GB)

( * ) Notice: Subject to any disclaimer, the term of this patent is extended or adjusted under 35 U.S.C. 154(b) by 0 days.

(21) Appl. No.: 14/388,948

(22) PCT Filed: Mar. 29, 2013

(86) PCT No.: PCT/IB2013/052545
§ 371 (c)(1),
(2) Date: Sep. 29, 2014

(87) PCT Pub. No.: WO2013/144916
PCT Pub. Date: Oct. 3, 2013

(65) Prior Publication Data
US 2015/0119428 A1    Apr. 30, 2015

Related U.S. Application Data

(60) Provisional application No. 61/618,639, filed on Mar. 30, 2012.

(51) Int. Cl.

| | | |
|---|---|---|
| *C07C 233/55* | (2006.01) | |
| *C07C 275/02* | (2006.01) | |
| *C07C 229/60* | (2006.01) | |
| *C07C 235/38* | (2006.01) | |
| *C07D 213/82* | (2006.01) | |
| *C07C 65/05* | (2006.01) | |
| *C07C 65/10* | (2006.01) | |
| *C07C 65/03* | (2006.01) | |
| *C07C 229/56* | (2006.01) | |
| *C07D 275/06* | (2006.01) | |

(52) U.S. Cl.
CPC ............ *C07C 233/55* (2013.01); *C07C 65/03* (2013.01); *C07C 65/05* (2013.01); *C07C 65/10* (2013.01); *C07C 229/56* (2013.01); *C07C 229/60* (2013.01); *C07C 235/38* (2013.01); *C07C 275/02* (2013.01); *C07D 213/82* (2013.01); *C07D 275/06* (2013.01); *C07B 2200/13* (2013.01)

(58) Field of Classification Search
CPC ... C07C 233/55; C07C 65/03; C07C 229/56; C07C 65/10; C07C 65/05; C07C 275/02; C07C 235/38; C07C 229/60; C07D 275/06; C07D 213/82; C07B 2200/13
See application file for complete search history.

(56) References Cited

U.S. PATENT DOCUMENTS

| | | | | |
|---|---|---|---|---|
| 2009/0264664 A1* | 10/2009 | Endo | ................... | A61K 9/0014 549/402 |
| 2011/0136835 A1* | 6/2011 | Kitt | ...................... | A61K 31/167 514/262.1 |

FOREIGN PATENT DOCUMENTS

EP    1946753 A1    7/2008

OTHER PUBLICATIONS

International Search Report and Written Opinion in PCT Application No. PCT/IB2013/052545 dated Jul. 8, 2013.
International Preliminary Report on Patentability in PCT Application No. PCT/IB2013/052545 dated Oct. 9, 2014.
Kawabata et al.: "Novel Crystalline Solid Dispersion of Transilast with High Photostability and Improved Oral Bioavailability," European Journal of Pharmaceutical Sciences, vol. 39, No. 4, pp. 256-262, Feb. 19, 2010.
Schultheiss et al.: "Pharmaceutical Cocrystals and Their Physiochemical Properties," Crystal Growth & Design, vol. 9, No. 6, pp. 2950-2967, Jun. 3, 2009.

* cited by examiner

*Primary Examiner* — Sudhakar Katakam
(74) *Attorney, Agent, or Firm* — J.A. Lindeman & Co., PLLC

(57) ABSTRACT

Mew tranilast complexes and new tranilast cocrystais are disclosed. These include all tranilast nicotinamide complex, a 1:1 tranilast nicotinamide cocrystal, a 1:1 tranilast saccharin complex, a 1:1 tranilast saccharin cocrystal, a 1:1 tranilast gentisic acid complex, a 1:1 tranilast gentisic acid cocrystal, a 1:1 tranilast salicylic acid complex, a 1:1 tranilast salicylic acid cocrystal, a 1:1 tranilast urea complex, a 1:1 tranilast urea cocrystal, a 1:1 tranilast 4-amtnoben2oic acid complex, a 1:1 tranilast 4-am!nobers2oic acid cocrystal, a 1:1 tranilast 2,4-di'hydroxybenzoic acid complex and a 1:1 tranilast 2,4-dihydroxybenzoic acid cocrystal. Also disclosed are pharmaceutical compositions containing a tranilast complex or cocrystal of the invention and a pharmaceutically acceptable carrier. Methods of treatment using the tranilast complexes and cocrystais as well as the pharmaceutical compositions are disclosed.

8 Claims, 32 Drawing Sheets

TRANILAST COMPOSITIONS AND COCRYSTALS

CROSS REFERENCE TO RELATED APPLICATIONS

This application claims priority to U.S. Patent Application 61/618,639, filed Mar. 30, 2012; the disclosure of which is incorporated herein by reference.

FIELD OF THE INVENTION

The invention relates to new tranilast compositions and tranilast cocrystals. The invention also relates to therapeutic uses of the new tranilast compositions or cocrystals as well as pharmaceutical compositions containing them.

BACKGROUND

Tranilast, (2-[[3-(3,4-dimethoxyphenyl)-1-oxo-2-propenyl]amino]benzoic acid), shown below, is a therapeutic agent that exhibits an anti-allergic effect. It has been shown to inhibit the release of inflammatory mediators, such as histamine, from mast cells and basophils (P. Zampini. *Int J Immunopharmacol.* 1983; 5(5): 431-5). Tranilast has been used as an anti-allergic treatment, for several years in Japan and South Korea, for conditions such as allergic conjunctivitis, bronchial asthma, allergic rhinitis and atopic dermatitis.

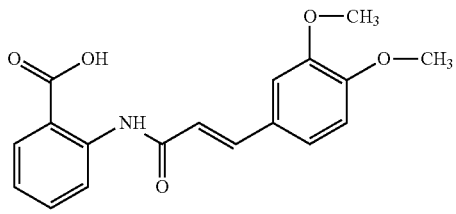 [SMILES: COc1ccc(/C=C/C(=O)Nc2ccccc2C(=O)O)cc1OC]

Tranilast is currently marketed in Japan and South Korea by Kissei Pharmaceutical Co. Ltd under the Rizaben® brand name. As well as displaying an anti-allergic effect tranilast has been shown to possess anti-proliferative properties. Tranilast was found to inhibit the proliferation of fibroblasts and suppress collagen synthesis (M. Isaji. *Biochem Pharmacol.* 1987; 36: 469-474) and also to inhibit the transformation of fibroblasts to myofibroblasts and their subsequent contraction (M. Isaji. *Life Sci.* 1994; 55: 287-292). On the basis of these effects tranilast is now also indicated for the treatment of keloids and hypertrophic scars. Its anti-fibrotic action is believed to be due to its ability to inhibit transforming growth factor beta (TGF-β) (H. Suzawa. *Jpn J Pharmacol.* 1992 October; 60(2): 91-96). TGF-β induced fibroblast proliferation, differentiation and collagen synthesis are known to be key factors in the progression of idiopathic pulmonary fibrosis and tranilast has been shown in-vivo to have potential in the treatment of this chronic lung disease (T. Jiang. *Afr J Pharm Pharmaco.* 2011; 5(10): 1315-1320). Tranilast has also been shown in-vivo to be have potential beneficial effects in the treatment of airway remodelling associated with chronic asthma (S. C. Kim. *J Asthma* 2009; 46(9): 884-894.

It has been reported that tranilast also has activity as an angiogenesis inhibitor (M. Isaji. *Br. J Pharmacol.* 1997; 122(6): 1061-1066). The results of this study suggested that tranilast may be beneficial for the treatment of angiogenic diseases such as diabetic retinopathy and age related macular degeneration. As well as showing inhibitory effects on mast cells and fibroblasts, tranilast has also demonstrated an ability to diminish tumor necrosis factor-alpha (TNF-α) from cultured macrophages (H. O. Pae. *Biochem Biophys Res Commun.* 371: 361-365) and T-cells (M. Platten. *Science.* 310: 850-855), and inhibited NF-kB-dependent transcriptional activation in endothelial cells (M. Spieker. *Mol Pharmacol.* 62: 856-863). Recent studies have revealed that tranilast attenuates inflammation and inhibits bone destruction in collagen induced arthritis in mice suggesting the possible usefulness of tranilast in the treatment of inflammatory conditions such as arthritis (N. Shiota. *Br. Pharmacol.* 2010; 159 (3): 626-635).

As has recently been demonstrated, in-vitro and in-vivo, tranilast also possesses an anti-tumor action. Tranilast has been shown to inhibit the proliferation, apoptosis and migration of several cell lines including breast cancer (R. Chakrabarti. *Anticancer Drugs.* 2009 June; 20(5): 334-45) and prostate cancer (S. Sato. *Prostate.* 2010 February; 70(3): 229-38) cell lines. In a study of mammary carcinoma in mice tranilast was found to produce a significant reduction in metastasis (R. Chakrabarti. *Anticancer Drugs.* 2009 June; 20(5): 334-45). In a pilot study in humans, tranilast was shown to have the potential to improve the prognosis of patients with advanced castration-resistant prostate cancer (K. Izumi. *Anticancer Research.* 2010 July; 30: 73077-81).

It has been reported that tranilast has the ability to induce or enhance neurogenesis and, therefore, could be used as an agent to treat neuronal conditions such as cerebral ischemia, glaucoma, multiple sclerosis, amyotrophic lateral sclerosis, Alzheimer's disease, neurodegenerative trinucleotide repeat disorders, neurodegenerative lysosomal storage diseases, spinal cord injury and trauma, dementia, schizophrenia and peripheral neuropathy (A. Schneider. EP2030617).

Tranilast's beneficial properties have been reported to have utility in several ocular conditions. Tranilast is currently approved in Japan and Korea far the treatment of allergic conjunctivitis. WO2010137681 claims the use of tranilast as a prophylactic or therapeutic agent for the treatment of retinal diseases. The anti-fibrotic properties of tranilast have been reported to be of benefit in maintaining the filtering blob during glaucoma surgery and this has been demonstrated in a pilot study in humans (E. Chihara. *J Glaucoma.* 1999; 11(2): 127-133). There have also been several reported cases of the beneficial use of tranilast in the prevention of postoperative recurrence of pterygium (C. Fukui. *Jap J Opthalmol.* 1999; 12: 547-549). Tsuji recently reported that tranilast may be beneficial not only in the prevention of pterygium recurrence, but also for the inhibition of symblepharon and granuloma formation (A. Tsuji. *Tokai J Exp Clin Med.* 2011; 36(4): 120-123). Collectively it has been demonstrated that tranilast possesses anti-allergic, anti-fibrotic, anti-inflammatory, anti-tumor, neurogenesis enhancing end angiogenesis inhibitory properties and as such may be useful for the treatment of diseases associated with such properties.

Tranilast occurs as a yellow crystalline powder that is identified by CAS Registry Number: 53902-12-8. As is typical of cinnamic acid derivatives (G. M. J. Schmidt *J Chem. Soc.* 1964: 2000) tranilast is photochemically unstable when in solution, transforming into cis-isomer and dimer forms on exposure to light (N. Hori. *Cehm Pharm Bull.* 1999; 47: 1713-1716). Although pure crystalline tranilast is photochemically stable in the solid state it is practically insoluble in water (14.5 µg/ml) and acidic media (0.7 µg/ml in pH 1.2 buffer solution) (Society of Japanese Pharmacopoeia. 2002). Although tranilast has shown activity in various indications, it is possible that the therapeutic potential of the drug is currently limited by its poor solubility and photostability. High energy amorphous forms are often used as a means of improving the solubility of poorly soluble APIs, however, literature shows that amorphous solid dispersions of tranilast are not completely photostable in the solid state and that they undergo photodegradation on storage when exposed to light (S. Onoue. *Eur J Pharm Sci.* 2010; 39: 256-262). US20110136835 describes a combination of tranilast and allopurinol and its use in the treatment of hyperuricemia associated with gout and has one mention of a "co-crystal form", but lacks any further description or characterization.

There is a need therefore to develop tranilast compositions that have improved solubility and/or photostability. A new tranilast composition and/or cocrystal of the invention answers one or both of these needs. A new tranilast composition and/or cocrystal of the invention may have other beneficial properties such as increased solubility, improved dissolution, and/or increased bioavailability when compared to tranilast itself.

Although therapeutic efficacy is the primary concern for an active pharmaceutical ingredient (API), the chemical composition and solid state form (i.e., the crystalline or amorphous form) of the API can be critical to its pharmacological properties, such as bioavailability, and to its development as a viable drug candidate. Compositions and crystalline forms of some API's have been used to alter the API's physicochemical properties. Each composition or crystalline form can have different solid state (physical and chemical) properties. The differences in physical properties exhibited by a novel solid state forms (such as, for example, a polymorph of the API or a cocrystal containing the API, discussed below) may affect pharmaceutical and pharmacological properties such as storage stability, compressibility and density (important in formulation and product manufacturing), and/or solubility and dissolution rates (important factors in determining bioavailability). For example, the rate of dissolution of an active ingredient in a patient's stomach fluid may have therapeutic consequences since it impacts the rate at which an orally administered active ingredient may reach the patient's bloodstream. Because these practical properties are influenced by the solid state properties, e.g. the crystalline form of the API, they can impact the selection of a particular compound as an API, the ultimate pharmaceutical dosage form, the optimization of manufacturing processes, and absorption in the body.

Physical properties of an API also have a major influence on the ability to deliver a drug by a desired method. For example, if a drug is delivered by inhalation physical properties relating to the API as a particle, such as morphology, density, surface energy, charge, hygroscopicity, stability, dispersive properties and/or agglomeration, can come into play. The solid state form of the API, and as described below, cocrystals of the API, provide opportunities to address, engineer and/or improve upon one or more of such properties and thereby upon methods of delivery.

Obtaining crystalline forms of an API, when possible, is also extremely useful in drug development. It permits better characterization of the drug candidate's chemical and physical properties. Crystalline forms often have better chemical and physical properties than the API in its amorphous state. Moreover, finding the most adequate solid-state form for further drug development can reduce the time and the cost of that development.

It may be possible to achieve more desirable properties of a particular API by forming a cocrystal of the API. A cocrystal of an API is a distinct chemical composition of the API and coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC). As crystalline forms, cocrystals may possess more favorable solid state, physical, chemical, pharmaceutical and/or pharmacological properties or be easier to process than known forms or formulations of the API. For example, a cocrystal may have different dissolution and/or solubility properties than the API and can therefore be more effective in therapeutic delivery. New pharmaceutical compositions comprising a cocrystal of a given API may therefore have different or superior properties as compared to its existing drug formulations.

SUMMARY OF THE INVENTION

The invention relates to new tranilast complexes and new tranilast cocrystals. In particular, the invention relates to a 1:1 tranilast nicotinamide complex, a 1:1 tranilast nicotinamide cocrystal, a 1:1 tranilast saccharin complex, a 1:1 tranilast saccharin cocrystal, a 1:1 tranilast gentisic acid complex, a 1:1 tranilast gentisic acid cocrystal, a 1:1 tranilast salicylic acid complex, a 1:1 tranilast salicylic acid cocrystal, a 1:1 tranilast urea complex, a 1:1 tranilast urea cocrystal, a 1:1 tranilast 4-aminobenzoic acid complex, a 1:1 tranilast 4-aminobenzoic acid cocrystal, a 1:1 tranilast 2,4-dihydroxybenzoic acid complex and a 1:1 tranilast 2,4-dihydroxybenzoic acid cocrystal. The invention relates to pharmaceutical compositions containing a tranilast complex or cocrystal of the invention and a pharmaceutically acceptable carrier. The tranilast complexes and cocrystals may be used in the same way as tranilast. Tranilast possesses anti-allergic, anti-fibrotic, anti-inflammatory, anti-tumor, neurogenesis enhancing and angiogenesis inhibitory properties and as such may be useful for the treatment of the diseases, disorders and conditions associated with such properties, as discussed above.

DETAILED DESCRIPTION

Figure 1:
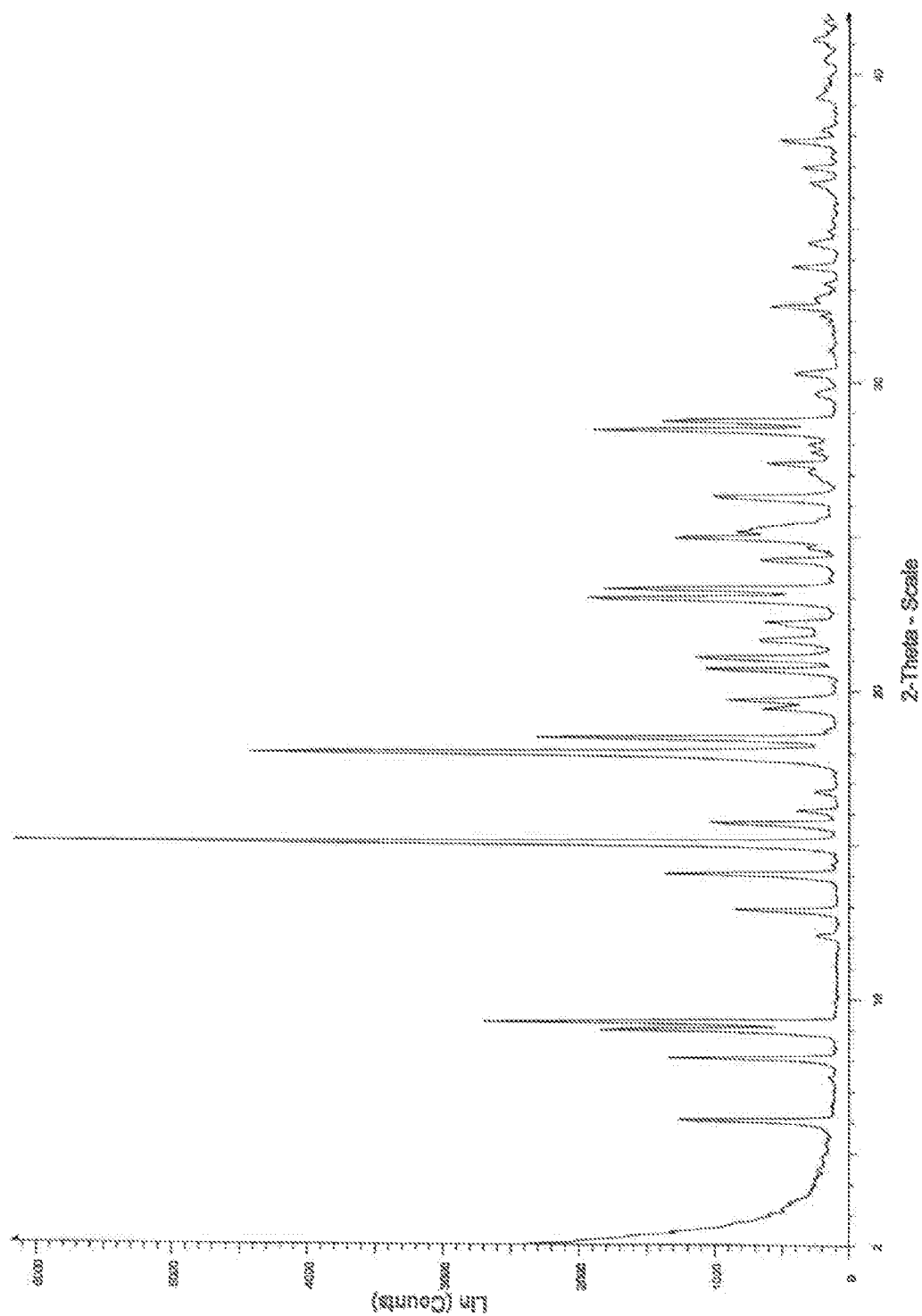
FIG. 1 shows an XRPD diagram of the 1:1 tranilast nicotinamide cocrystal.

The invention relates to new tranilast complexes and new tranilast cocrystals. In particular, the invention relates to a 1:1 tranilast nicotinamide complex, a 1:1 tranilast nicotinamide cocrystal, a 1:1 tranilast saccharin complex, a 1:1 tranilast saccharin cocrystal, a 1:1 tranilast gentisic acid complex, a 1:1 tranilast gentisic acid cocrystal, a 1:1 tranilast salicylic acid complex, a 1:1 tranilast salicylic acid cocrystal, a 1:1 tranilast urea complex, a 1:1 tranilast urea cocrystal, a 1:1 tranilast aminobenzoic acid complex, a 1:1 tranilast 4-aminobenzoic acid cocrystal, a 1:1 tranilast 2,4-dihydroxybenzoic acid complex and a 1:1 tranilast 2,4-dihydroxybenzoic acid cocrystal. The invention relates to pharmaceutical compositions containing a tranilast complex or cocrystal of the invention and a pharmaceutically acceptable carrier. The tranilast complexes and cocrystals and methods used to characterize them are described below.

Therapeutic Uses of Tranilast Complexes and Cocrystals

The invention further relates to the therapeutic use of the tranilast complexes and cocrystals of the invention, 1:1 tranilast nicotinamide complex, a 1:1 tranilast nicotinamide cocrystal, a 1:1 tranilast saccharin complex, a 1:1 tranilast saccharin cocrystal, a 1:1 tranilast gentisic acid complex, a 1:1 tranilast gentisic acid cocrystal, a 1:1 tranilast salicylic acid complex, a 1:1 tranilast salicylic acid cocrystal, a 1:1 tranilast urea complex, a 1:1 tranilast urea cocrystal, a 1:1 tranilast 4-aminobenzoic acid complex, a 1:1 tranilast 4-aminobenzoic acid cocrystal, a 1:1 tranilast 2,4-dihydroxybenzoic acid complex and a 1:1 tranilast 2,4-dihydroxybenzoic acid cocrystal. Tranilast, as discussed above, is known to possess anti-allergic, anti-fibrotic, anti-inflammatory, anti-tumor, neurogenesis enhancing and angiogenesis inhibitory properties. The tranilast complexes and cocrystals of the invention may then be used, in the same way as tranilast, to treat diseases, disorders and conditions, such as those discussed above, that are associated with such properties. Accordingly, the invention relates to the method of treating such a disease, disorder, or condition comprising the step of administering to a patient in need thereof a therapeutically effective amount of a tranilast complex or cocrystal of the invention or of administering to a patient in need thereof a therapeutic composition containing a tranilast complex or cocrystal of the invention.

The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

Pharmaceutical Compositions Containing the Tranilast Complexes and Cocrystals

The invention also relates to pharmaceutical compositions comprising a therapeutically effective amount of a tranilast complex or cocrystal according to the invention and a pharmaceutically acceptable carrier (also known as a pharmaceutically acceptable excipient). As mentioned above, these pharmaceutical compositions are therapeutically useful to treat or prevent disorders such as those discussed above.

A pharmaceutical composition of the invention may be in any pharmaceutical form which contains a tranilast complex or cocrystal according to the invention. The pharmaceutical composition may be, for example, a tablet, a capsule, a liquid suspension, an injectable composition, a topical composition, an inhalable composition or a transdermal composition. Liquid pharmaceutical compositions may be prepared comprising a tranilast complex of the invention. The pharmaceutical compositions generally contain, for example, about 0.1% to about 99.9% by weight of a tranilast complex or cocrystal of the invention, for example, about 0.5% to about 99% by weight of a tranilast complex or cocrystal of the invention and, for example, 99.5% to 0.5% by weight of at least one suitable pharmaceutical excipient. In one embodiment, the composition may be between about 5% and about 75% by weight of a tranilast complex or cocrystal of the invention with the rest being at least one suitable pharmaceutical excipient or at least one other adjuvant, as discussed below.

A "therapeutically effective amount of a tranilast complex or cocrystal according to the invention" is that which correlates to the therapeutic effect currently achieved when administering orally about 50-about 600 mg of tranilast itself. As discussed above, tranilast is marketed in Japan and South Korea by Kissei Pharmaceutical Co. Ltd under the Rizaben® brand name. Tranilast is prescribed orally to treat bronchial asthma, allergic rhinitis, atopic dermatitis, keloid or hypertrophic scar. The typical dosage in adults is currently one 100 mg tablet three times per day. Up until now tranilast has been used orally in very high quantities. This is because the oral bioavailability of the drug is likely to be extremely low. Firstly, as discussed above, tranilast is so insoluble that only a tiny amount is absorbed in the gastrointestinal system. But secondly a large proportion of the absorbed drug is then removed by first pass metabolism. The absolute bioavailability in humans is not known, but a pharmacokinetic study in rats showed that the relative bioavailability of crystalline tranilast administered orally compared to IV administration was only 1.2% (S. Onoue. *Drug Metab Pharmacokinet.* 2012). A tranilast complex or cocrystal of the invention having improved solubility and also delivered systemically by a means that avoids first pass metabolism (sublingual, buccal, IV, topical, inhaled, ophthalmic) can achieve the same efficacy as is currently known for tranilast with a significantly lower dose, even as low as about 1-2 mg. Thus, a therapeutically effective amount of a tranilast complex or cocrystal of the invention may be in the range mentioned above but may also range from about 0.5 mg to about 250 mg, and even from about 1 mg to about 100 mg of the tranilast complex or cocrystal itself. The therapeutically effective amount of a drug can also depend upon the route of administration as is known in the art. For example, in a topical application such as with a cream, eye drops, or in pulmonary delivery the therapeutically effective amount may be small.

The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion of tranilast; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a solid pharmaceutical composition of the invention, that is one containing a tranilast cocrystal of the invention, a carrier should be chosen that maintains the crystalline form. In other words, the carrier in a solid pharmaceutical composition should not substantially alter the tranilast cocrystal. Nor should the carrier be otherwise incompatible with the tranilast cocrystal used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a tranilast complex or cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing a tranilast complex or cocrystal of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active tranilast complexes and cocrystals of the invention topically to the lung. One such means could involve a dry powder inhaler formulation of respirable particles comprised of the tranilast complexes or cocrystals of the invention, which the patient being treated inhales. It is common for a dry powder formulation to include carrier particles, to which the tranilast complex or cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose. The tranilast complex or cocrystal would be dispersed into the respiratory tract, and subsequently contact the lower lung in a pharmaceutically effective amount.

Another means of administering the active compounds topically to the eyes of the subject would involve administering a topical liquid/liquid suspension in the form of eye drops or eye wash. Liquid pharmaceutical compositions of the active compound for producing an eye drop or eye wash formulation can be prepared by combining the active compound with a suitable vehicle, such as sterile pyrogen free water or sterile saline by techniques known to those skilled in the art.

In addition to the topical method of administration described above, there are various methods of administering the active tranilast complexes and cocrystals of the invention systemically by such methods. One such means would involve an aerosol suspension of respirable particles comprised of the tranilast complexes or cocrystals of the invention, which the patient being treated inhales. The tranilast complex or cocrystal would be absorbed into the bloodstream via the lungs in a pharmaceutically effective amount. The respirable particles can be liquid or solid, with a particle size sufficiently small to pass through the mouth and larynx upon inhalation.

Because the crystalline form of a tranilast cocrystal may be maintained during preparation, solid dosage forms are preferred for the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier). A tranilast complex and cocrystal according to the invention may also be used to formulate liquid or injectable pharmaceutical compositions. Administration of a tranilast complex or cocrystal in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

EXAMPLES

The following analytical methods were used to characterize the tranilast complexes and cocrystals of the invention. For work done at room temperature (RT) that is generally about 25° C.

X-Ray Powder Diffraction Characterisation:

X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected over an angular range of 2° to 42° 2Θ using a step size of 0.05° 2Θ and a step time of 0.5 seconds. Samples run under ambient conditions were prepared as flat plate specimens using powder as received without grinding. Approximately, 35 mg of the sample was gently packed into a cavity cut into polished, zero background (510) silicon wafer. All samples were analyzed using Diffrac Plus EVA v11.0.0.2 or v13.0.0.2.

Single Crystal X-Ray Diffraction (SCXRD):

Data were collected on an Oxford Diffraction SuperNova Dual source, Cu at zero, Atlas CCD Diffractometer equipped with an Oxford Cryosystems Cryostream cooling device.

Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning Calorimetry (DSC):

DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C.·min$^{-1}$ from 30 to 350° C. A purge of dry nitrogen at 60 ml·min$^{-1}$ was maintained over the sample. The instrument control, data acquisition and analysis were performed with Pyris Software v9.0.1.0203.

Thermo-Gravimetric Analysis (TGA):

TGA data were collected on a PerkinElmer Pyris 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° C.·min$^{-1}$ from ambient temperature to 400° C. A nitrogen purge at 20 ml·min$^{-1}$ was maintained over the sample. The instrument control, data acquisition and analysis were performed with Pyris Software v9.0.1.0203.

Solution Proton NMR:

$^1$H-NMR spectra were collected using a JEOL EX 270 MHz spectrometer equipped with an auto-sampler. The samples were dissolved in d6-DMSO for analysis. The data was acquired using Delta NMR Processing and Control Software version 4.3.

Stability Study X-Ray Powder Diffraction Characterisation:

X-Ray Powder Diffraction patterns at the required time points were collected on a PANalytical diffractometer using Cu Kα radiation (45 kV, 40 mA), θ-θ goniometer, focusing mirror, divergence slit (½″), soller slits at both incident and divergent beam (4 mm) and a PIXcel detector. The software used for data collection was X'Pert Data Collector, version 2.2f and the data was presented using X'Pert Data Viewer, version 1.2d. Instrument verification was performed using a silicon and benzoic acid standard, performed with the same batch program as listed below for sample analysis. Samples were run under ambient conditions and were analyzed by transmission foil XRPD, using the powder as received. Approximately 2-5 mg of the sample was mounted on a 96 position sample plate supported on a polyimide (Kapton, 12.7 μm thickness) film. Plate height (Z) was set to 9 mm. Data was collected in the range 3-40° 2θ with a continuous scan (speed of 0.2° 2θ/s).

Example 1

1:1 Tranilast Nicotinamide Cocrystal 1.1 Preparation of a 1:1 Tranilast Nicotinamide Cocrystal The batch of the 1:1 tranilast nicotinamide cocrystal used for characterisation was prepared as follows:

Tranilast (100 mg) and nicotinamide (37.3 mg) were weighed into a glass vial. Isopropyl acetate (1.5 ml) was added to the vial. The resulting yellow slurry was placed in a shaker and matured for 5 days (room temperature (RT, ~25° C.) to 50° C. on an 8 hour cycle, heating to 50° C. for 4 hours and then cooling to RT for a further 4 hours). The product was then filtered under vacuum and the resulting colourless crystals were dried under ambient conditions overnight.

1.2 XRPD Characterisation of a 1:1 Tranilast Nicotinamide Cocrystal

The experimental XRPD pattern of the 1:1 tranilast nicotinamide cocrystal is shown in FIG. 1. Table 1 lists the angles, °2θ±0.2°2θ, and d-spacing of the peaks identified in the experimental XRPD pattern of FIG. 1. The entire list of peaks, or a subset thereof, may be sufficient to characterize the cocrystal, as well as by an XRPD pattern substantially similar to FIG. 1. For example, a 1:1 tranilast nicotinamide cocrystal of the invention may be characterised by a powder X-ray diffraction pattern having at least three peaks selected from 6.0, 8.0, 12.0, 15.0 and 15.6 °2θ±0.2°2θ.

TABLE 1

| Angle °2θ ± 0.2 °2θ | d value Angstrom | Intensity % |
| --- | --- | --- |
| 6.0 | 14.63 | 20.3 |
| 8.0 | 11.02 | 21.5 |
| 9.0 | 9.85 | 29.6 |
| 9.2 | 9.60 | 43.6 |
| 12.0 | 7.35 | 3.7 |
| 12.9 | 6.87 | 13.7 |
| 14.0 | 6.31 | 21.9 |
| 15.0 | 5.89 | 100.0 |
| 15.6 | 5.66 | 16.5 |
| 16.1 | 5.50 | 6.1 |
| 16.7 | 5.29 | 4.0 |
| 18.0 | 4.94 | 71.6 |
| 18.4 | 4.81 | 37.4 |
| 19.4 | 4.56 | 10.2 |
| 19.7 | 4.51 | 14.5 |
| 20.7 | 4.29 | 17.1 |
| 21.1 | 4.21 | 18.4 |
| 21.6 | 4.10 | 10.5 |
| 22.2 | 4.00 | 9.9 |
| 22.9 | 3.87 | 31.2 |
| 23.3 | 3.82 | 29.2 |
| 24.2 | 3.67 | 10.4 |
| 25.0 | 3.56 | 20.6 |
| 25.2 | 3.53 | 11.6 |
| 26.2 | 3.39 | 15.9 |
| 27.3 | 3.26 | 9.8 |
| 28.4 | 3.14 | 30.5 |
| 28.7 | 3.11 | 22.1 |
| 30.3 | 2.95 | 6.4 |
| 32.5 | 2.75 | 9.3 |
| 33.8 | 2.65 | 6.7 |
| 34.6 | 2.59 | 4.7 |
| 36.5 | 2.46 | 4.5 |
| 37.0 | 2.43 | 5.5 |
| 37.8 | 2.38 | 8.1 |

1.3 SCXRD Characterisation of a 1:1 Tranilast Nicotinamide Cocrystal

The crystal used for single crystal structure determination was prepared as follow: Approximately 20 mg (estimated by eye) of the 1:1 tranilast nicotinamide cocrystal batch prepared as previously described was placed in a glass HPLC vial and 1 ml of dichloromethane was added. The sample was placed on a shaker at 50° C. for ca. 30 minutes before being removed and quickly filtered into a clean glass vial. The vial was covered with film which was then pierced to allow slow evaporation and crystal formation. A suitable single crystal was isolated from the crystals that were formed by this method.

Figure 2:
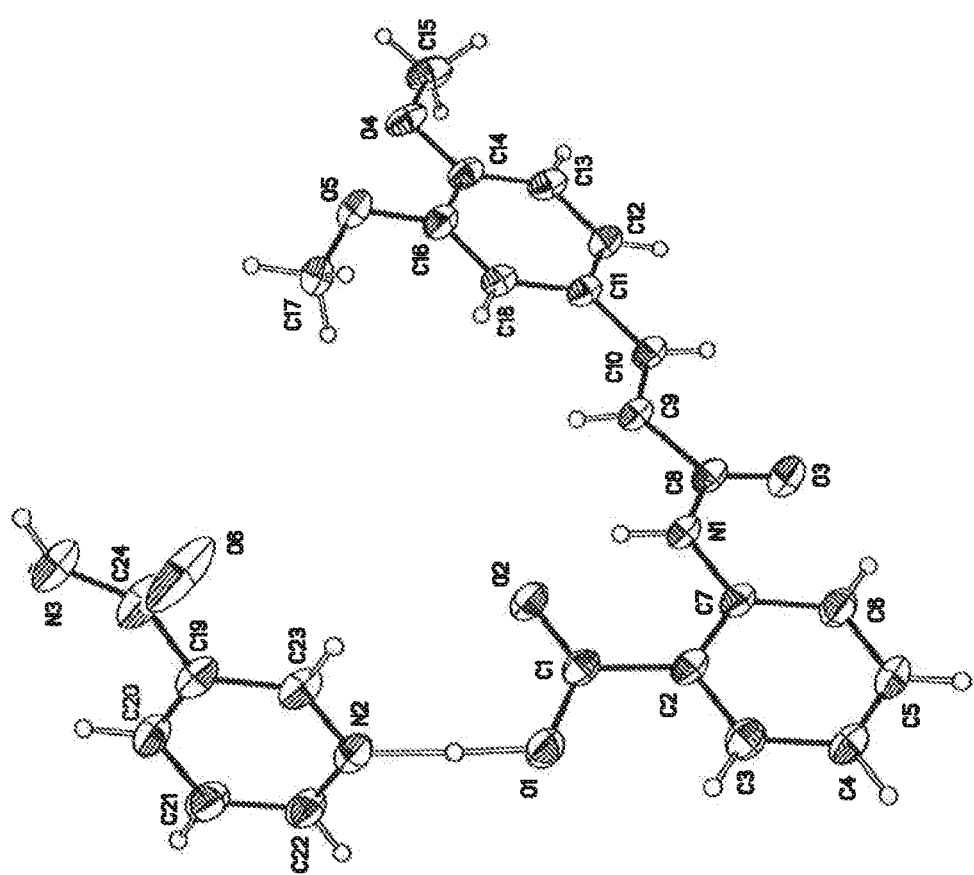
FIG. 2 shows an ORTEP drawing of the 1:1 tranilast nicotinamide cocrystal at 100 K.
Figure 3:
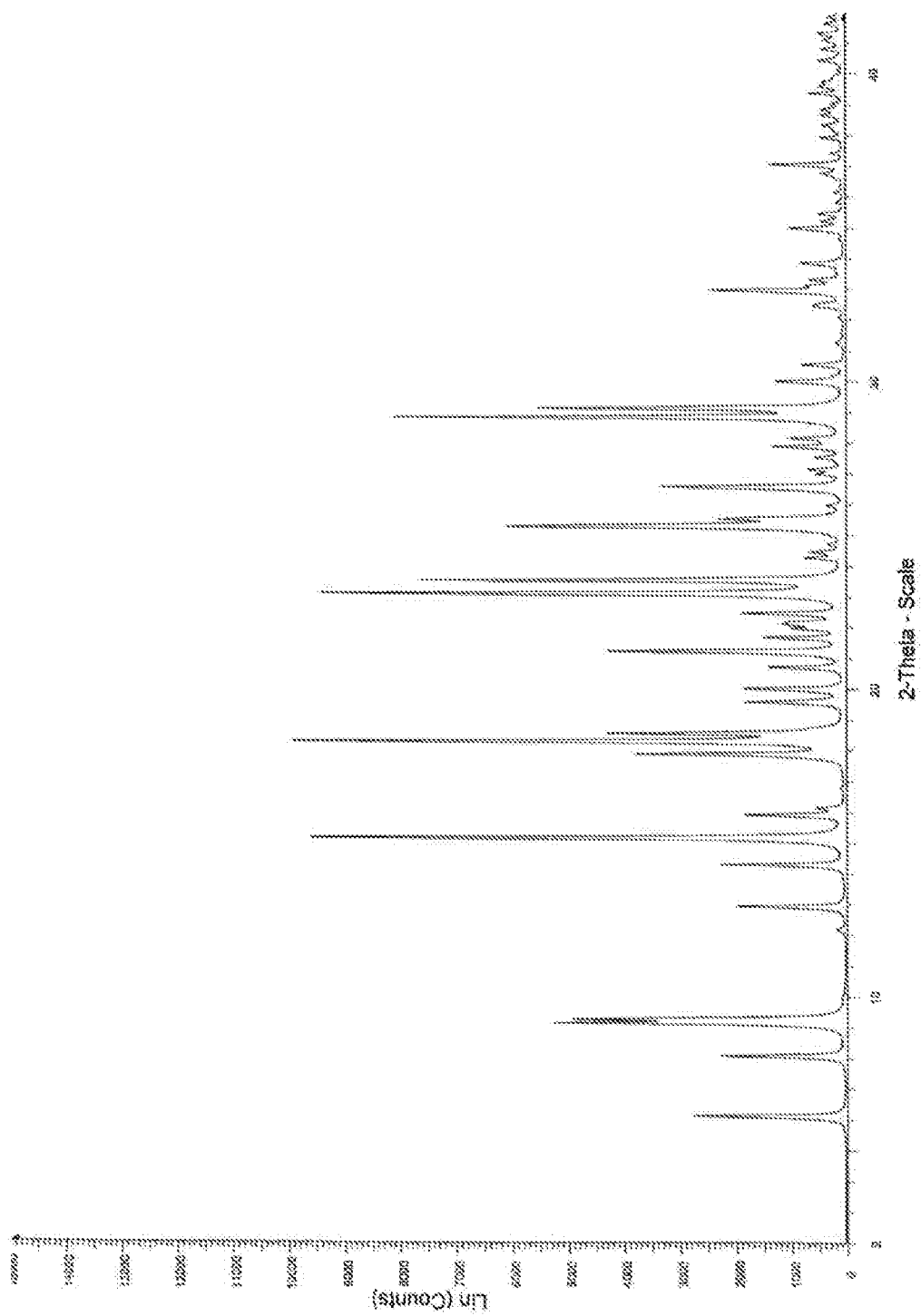
FIG. 3 shows a calculated XRPD pattern for the 1:1 tranilast nicotinamide cocrystal at 100 K.

The single crystal data and structure refinement parameters for the structure measured at 100 K are reported in Table 2, below. An ORTEP diagram of the 1:1 tranilast nicotinamide cocrystal at 100 K showing the numbering system employed is shown in FIG. 2. Anisotropic atomic displacement ellipsoids for the non-hydrogen atoms are shown at the 50% probability level and hydrogen atoms are displayed as spheres of arbitrary radius. The calculated XRPD pattern based on the single crystal data and structure for the 1:1 tranilast nicotinamide cocrystal at 100 K is shown in FIG. 3. It is also noted that there are some small temperature shifts in some of the peaks owing to the fact that the experimental XRPD pattern was collected at room temperature and the calculated XRPD pattern is derived from data collected at 100 K. There are also small intensity differences owing to preferred orientation effects, present in the experimental pattern.

TABLE 2

| | |
|---|---|
| Molecular formula | $C_{24}H_{23}N_3O_6$ |
| Molecular weight | 449.45 |
| Crystal System | Monoclinic |
| Space Group | P21/n |
| Unit Cell Dimensions | a = 5.1305(4) Å |
| | b = 19.3861(15) Å |
| | c = 21.976(2) Å |
| | α = 90.00° |
| | β = 90.320(9)° |
| | γ = 90.00° |
| Cell Volume | 2185.7(3) Å$^3$ |
| Z | 4 |
| Temperature | 100(1) K |
| Radiation Wavelength/type | 1.54178 Å/CuKα |
| Goodness of fit | 1.008 |
| R factor | 0.0584 |
| Morphology | Colourless needle |

1.4 DSC of the 1:1 Tranilast Nicotinamide Cocrystal

Figure 4:
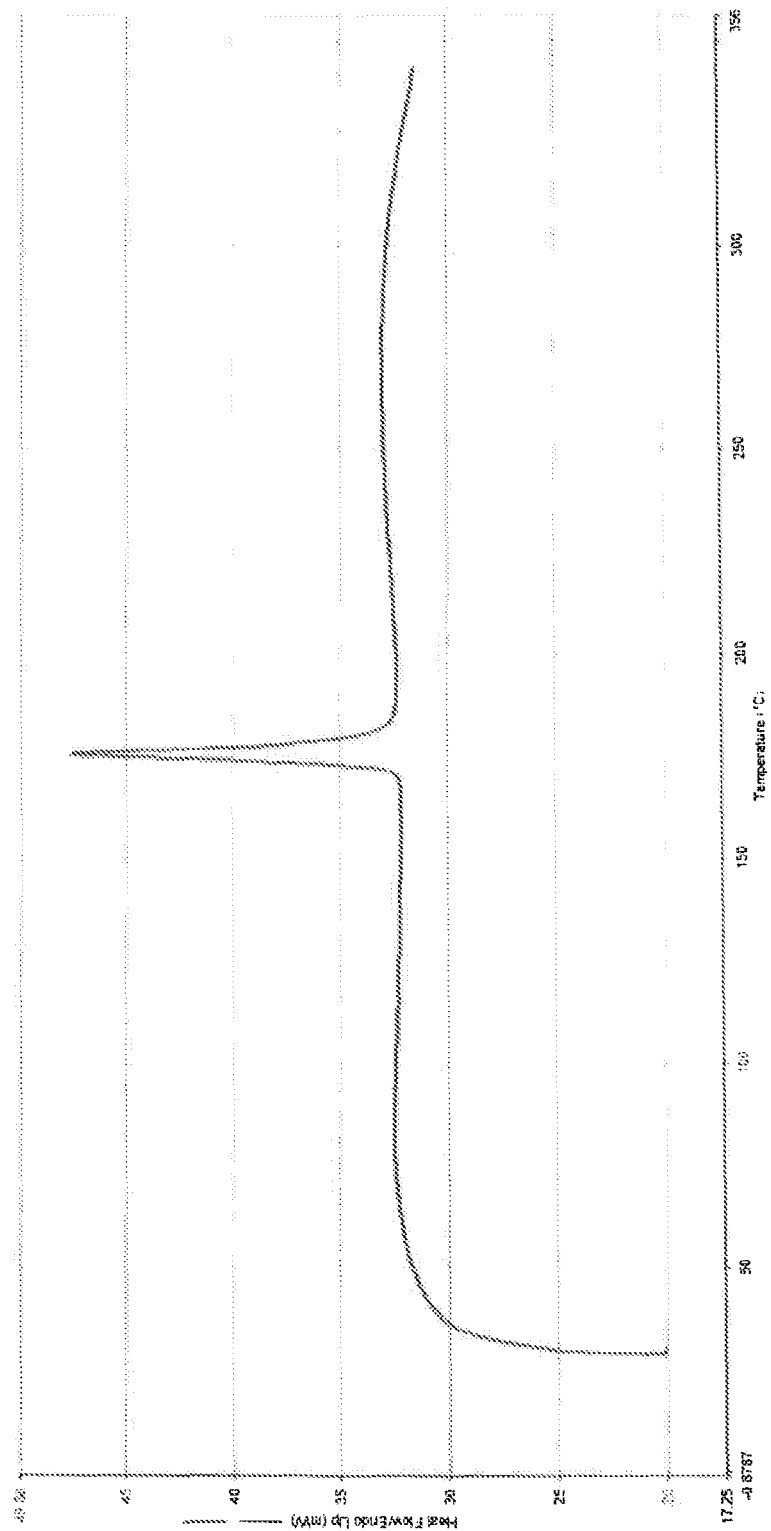
FIG. 4 shows a DSC trace for the 1:1 tranilast nicotinamide cocrystal.

The differential scanning calorimetry (DSC) trace, FIG. 4, shows a single endotherm with an onset temperature of 168.1° C. and a peak maximum of 175.4° C. corresponding to the melt of the cocrystal.

1.5 TGA of the 1:1 Tranilast Nicotinamide Cocrystal

Figure 5:
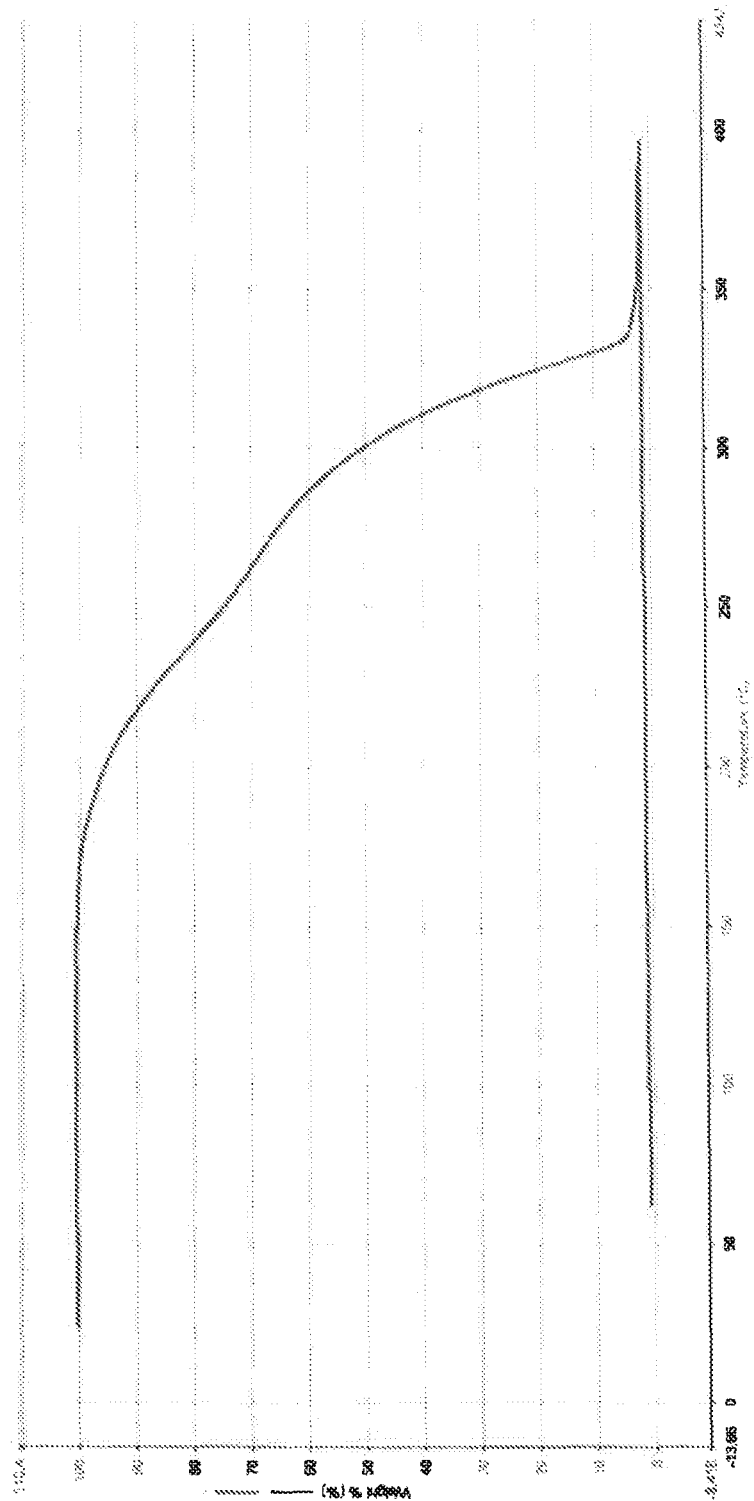
FIG. 5 shows a TGA trace for the 1:1 tranilast nicotinamide cocrystal.

The thermal gravimetric analysis (TGA) trace, FIG. 5, shows no significant weight loss prior to the cocrystal melt temperature with 99.7% weight remaining at 170° C. The TGA shows that there is a weight loss of 27% between 170 and 253° C. This corresponds to one molar equivalent of nicotinamide.

1.6 $^1$H NMR Spectrum of 1:1 Tranilast Nicotinamide Cocrystal

Figure 6:
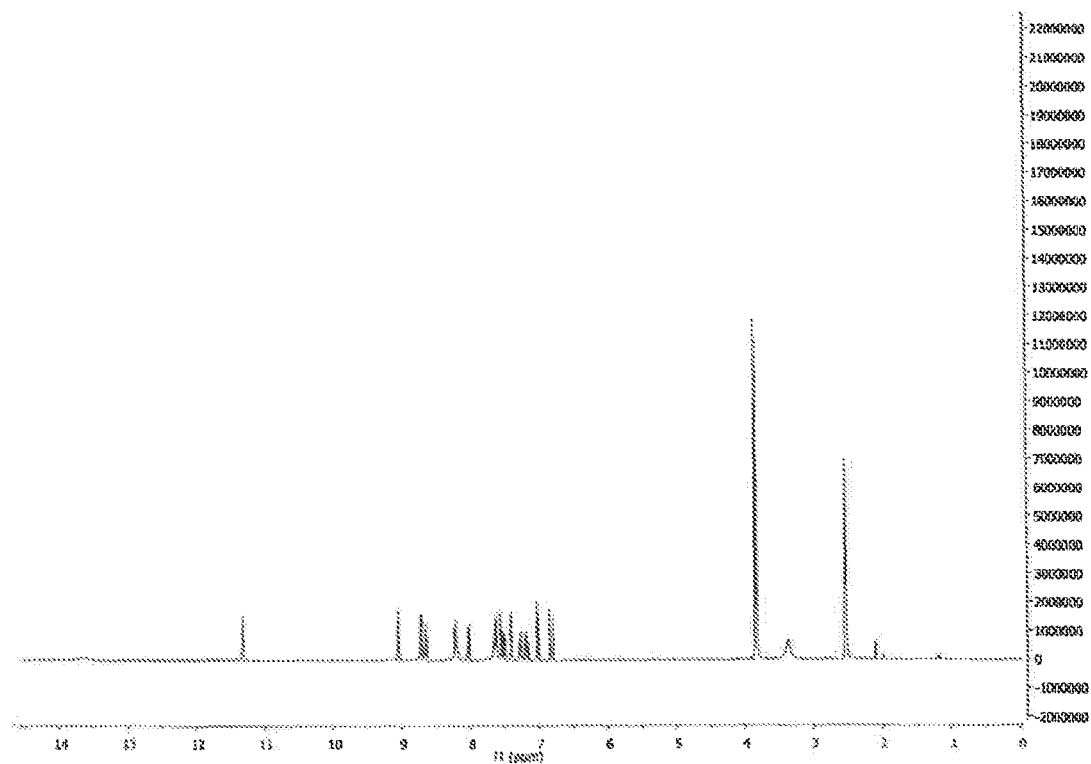
FIG. 6 shows the $^1$H NMR spectrum of 1:1 tranilast nicotinamide cocrystal.

The $^1$H NMR spectrum of the 1:1 tranilast nicotinamide cocrystal, shown in FIG. 6, displays the following peaks: $^1$H NMR (400 MHz, d6-DMSO) δ: 13.65 (1H), 11.31 (1H), 9.04 (1H), 8.71 (1H) 8.64 (1H), 8.22 (2H), 8.02 (2H), 7.48-7.66 (4H), 7.40 (1H), 7.26 (1H), 7.18 (1H), 7.01 (1H), 6.81 (1H), 3.84 (3H) and 3.81 (3 H). The peak at 9.04 ppm in the $^1$H NMR spectrum corresponds to one proton on the aromatic ring of nicotinamide. Comparison of the integration of this peak with that at 8.02 ppm, which corresponds to one of the aromatic protons of tranilast, indicates that the cocrystal has an API:coformer stoichiometry of 1:1.

1.7 Physical Stability Study of the 1:1 Tranilast Nicotinamide Cocrystal

Figure 7:
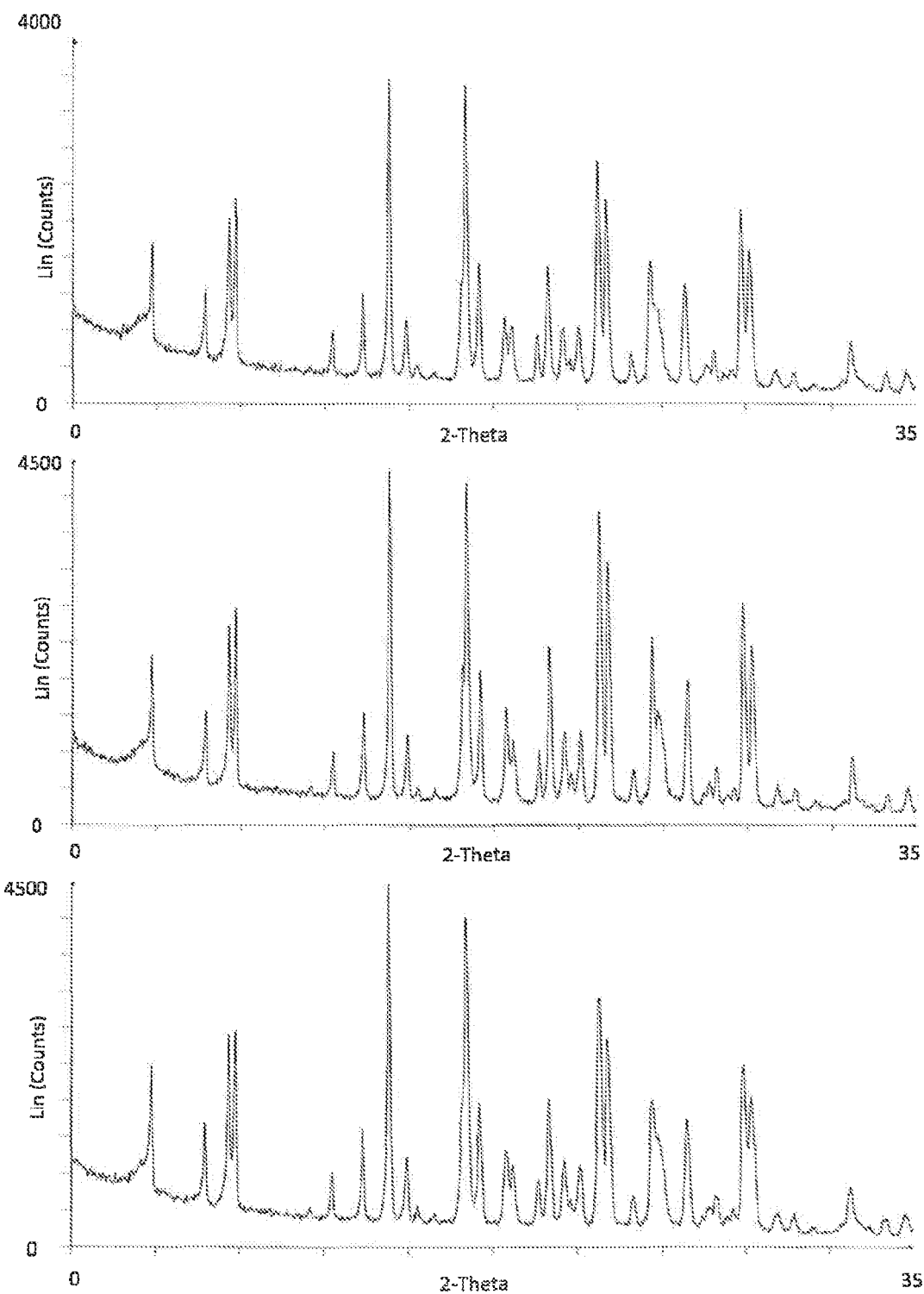
FIG. 7 shows an overlay of the XRPD patterns of the 1:1 tranilast nicotinamide cocrystal at various time points during a 6 month accelerated stability study at 40° C./75% RH.

A stability study was carried out to examine the physical stability of the 1:1 tranilast nicotinamide cocrystal with respect to dissociation into its starting components over time under accelerated conditions. Approximately 1-2 mg of the 1:1 tranilast nicotinamide cocrystal was placed in seven clear glass vials. The glass vials were loosely sealed with plastic screw caps so as to provide a barrier to solid transfer but to still allow moisture equilibration with the outer environment. The vial head space above the sample was estimated to be >95% of the total vial volume. All seven samples were then placed on a tray and stored within a stability cabinet set at 40° C./75% RH. The individual samples were removed from the cabinet at pre-determined time points as shown in Table 3 and examined by XRPD. At every time point examined the XRPD pattern obtained was characteristic of the 1:1 tranilast nicotinamide cocrystal with no evidence of either of the starting materials, or any new peaks to indicate conversion to a different crystalline form. FIG. 7 illustrates the XRPD patterns obtained at the time points 0, three months and six months. FIG. 7 is an overlay of the XRPD patterns of the 1:1 tranilast nicotinamide cocrystal at those time points during a 6 month accelerated stability study at 40° C./75% RH. It can be seen that there is no obvious change within the sample over the six month period and that there is no evidence of dissociation into either of the starting materials, or conversion into another crystalline form of tranilast, indicating that the 1:1 tranilast nicotinamide cocrystal is stable under these conditions.

TABLE 3

| Time Point | XRPD Characterization |
|---|---|
| 0 | cocrystal |
| 1 week | cocrystal |
| 2 week | cocrystal |
| 3 week | cocrystal |
| 1 month | cocrystal |
| 2 months | cocrystal |
| 3 months | cocrystal |
| 6 months | cocrystal |

Example 2

1:1 Tranilast Saccharin Cocrystal 2.1 Preparation of a 1:1 Tranilast Saccharin Cocrystal The batch of the 1:1 tranilast saccharin cocrystal used for characterisation was prepared as follows:

Tranilast (250 mg) and saccharin (140 mg) were weighed into a glass vial. Dichloromethane (2.0 ml) was added to the vial. The resulting yellow slurry was placed in a shaker and matured for 5 days (RT to 50° C. on an 8 hour cycle, heating to 50° C. for 4 hours and then cooling to RT for a further 4 hours). The product was then filtered under vacuum dried under ambient conditions overnight.

2.2 XRPD Characterisation of a 1:1 Tranilast Saccharin Cocrystal

Figure 8:
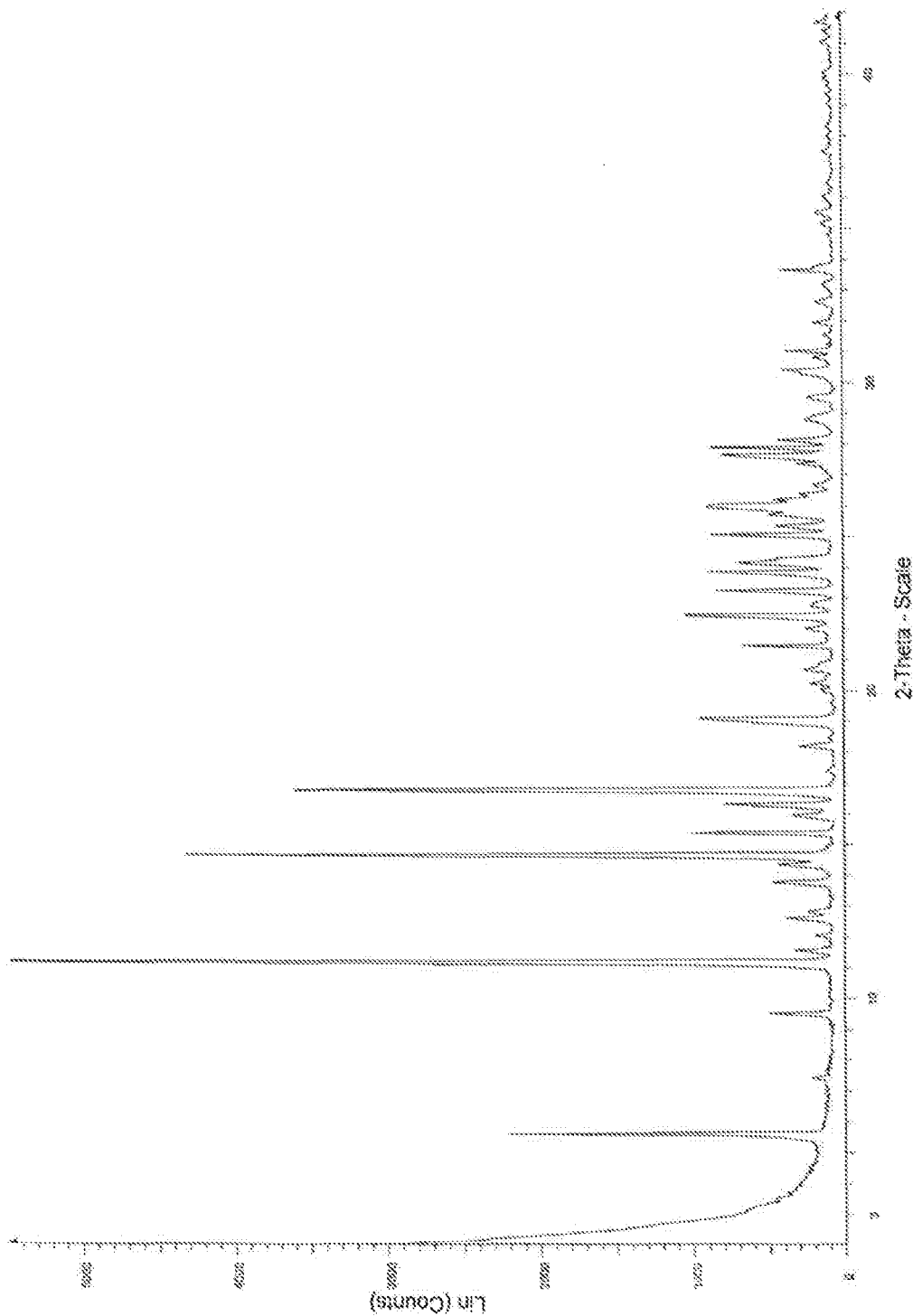
FIG. 8 shows an XRPD diagram of the 1:1 tranilast saccharin cocrystal.

The experimental XRPD pattern of the 1:1 tranilast saccharin cocrystal is shown in FIG. 8. Table 4 lists the angles, °2θ±0.2°2θ, and d-spacing of the peaks identified in the experimental XRPD pattern of FIG. 8. The entire list of peaks, or a subset thereof, may be sufficient to characterize the cocrystal, as well as by an XRPD pattern substantially similar to FIG. 8. For example, a 1:1 tranilast saccharin cocrystal of the invention may be characterised by a powder X-ray diffraction pattern having at least three peaks selected from 5.6, 9.5, 14.6, 15.4, 16.2 and 16.7 °2θ±0.2°2θ.

TABLE 4

| Angle °2θ ± 0.2 °2θ | d value Angstrom | Intensity % |
|---|---|---|
| 5.6 | 15.91 | 28.5 |
| 7.4 | 12.02 | 2.8 |
| 9.5 | 9.35 | 6.4 |
| 11.1 | 7.94 | 100.0 |
| 11.5 | 7.68 | 4.1 |
| 12.1 | 7.34 | 2.4 |
| 12.5 | 7.05 | 4.9 |
| 12.8 | 6.89 | 3.0 |
| 13.8 | 6.43 | 6.1 |
| 14.3 | 6.17 | 5.5 |
| 14.6 | 6.06 | 55.8 |
| 15.4 | 5.76 | 12.9 |
| 15.9 | 5.57 | 4.4 |
| 16.2 | 5.45 | 10.1 |
| 16.7 | 5.29 | 46.5 |
| 18.2 | 4.88 | 3.7 |
| 19.0 | 4.66 | 12.2 |
| 20.2 | 4.39 | 2.7 |
| 20.7 | 4.29 | 3.3 |
| 21.4 | 4.14 | 8.5 |
| 22.0 | 4.03 | 3.1 |
| 22.4 | 3.96 | 13.3 |
| 22.8 | 3.90 | 2.7 |
| 23.2 | 3.83 | 10.7 |
| 23.8 | 3.74 | 11.3 |
| 24.1 | 3.69 | 8.8 |
| 25.0 | 3.56 | 11.2 |
| 25.3 | 3.51 | 5.6 |
| 25.7 | 3.47 | 6.1 |
| 25.9 | 3.43 | 11.4 |
| 26.7 | 3.34 | 2.4 |
| 27.3 | 3.26 | 3.7 |
| 27.6 | 3.23 | 10.1 |
| 27.9 | 3.20 | 11.1 |
| 28.1 | 3.17 | 5.4 |
| 28.8 | 3.09 | 3.0 |
| 29.5 | 3.03 | 2.8 |
| 30.4 | 2.94 | 5.0 |
| 30.8 | 2.90 | 2.4 |
| 31.0 | 2.88 | 4.6 |
| 32.0 | 2.80 | 2.4 |
| 33.7 | 2.66 | 5.1 |

2.3 DSC of the 1:1 Tranilast Saccharin Cocrystal

Figure 9:
FIG. 9 shows a DSC trace for the 1:1 tranilast saccharin cocrystal.

The differential scanning calorimetry (DSC) trace, FIG. 9, shows a single endotherm with an onset temperature of 169.7° C. and a peak maximum of 183.1° C. corresponding to the melt of the cocrystal.

2.4 TGA of the 1:1 Tranilast Saccharin Cocrystal

Figure 10:
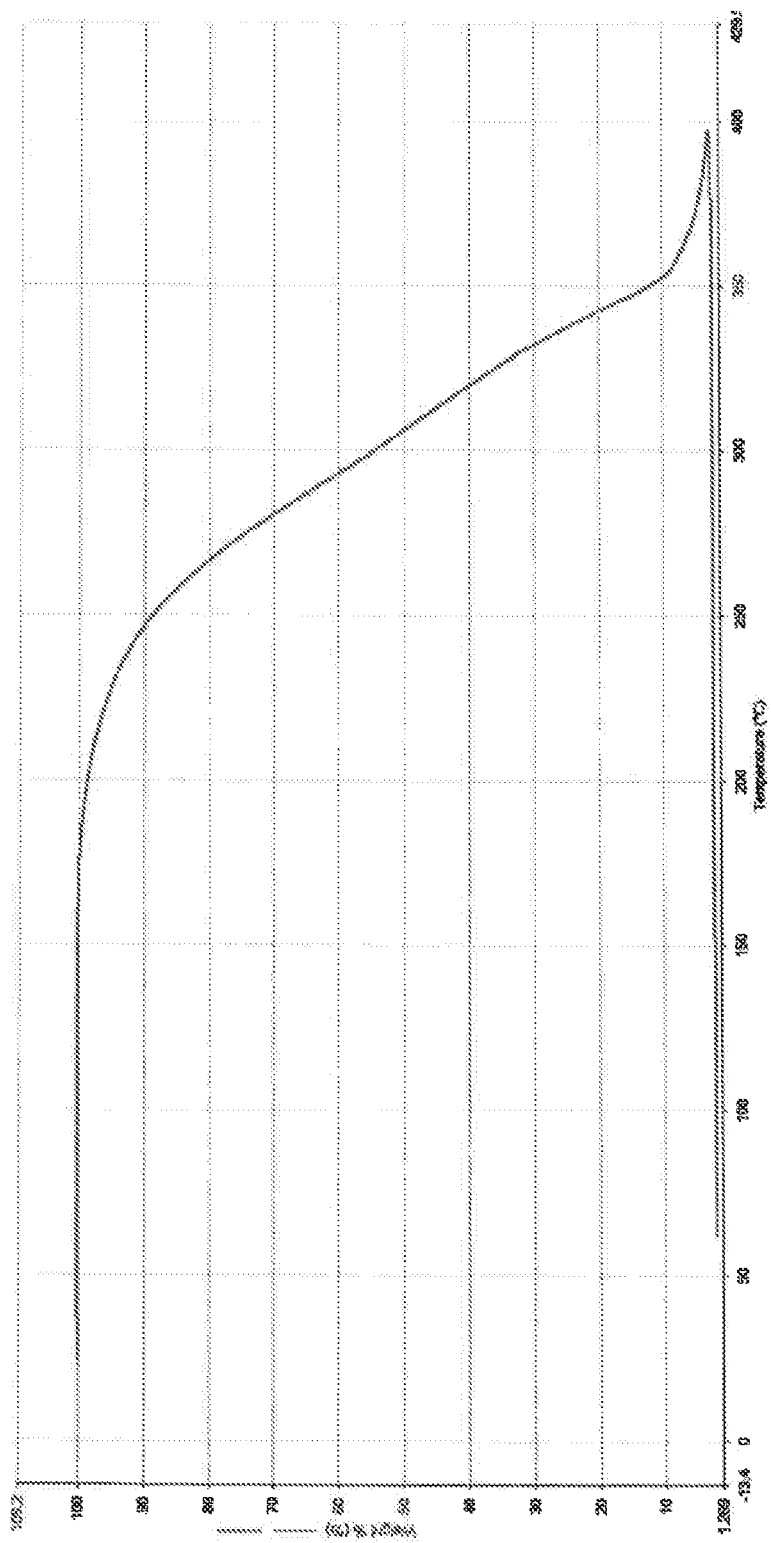
FIG. 10 shows a TGA trace for the 1:1 tranilast saccharin cocrystal.

The thermal gravimetric analysis (TGA) trace, FIG. 10, shows no significant weight loss prior to the cocrystal melt temperature with 99.8% weight remaining at 180° C.

2.5 $^1$H NMR Spectrum of the 1:1 Tranilast Saccharin Cocrystal

Figure 11:
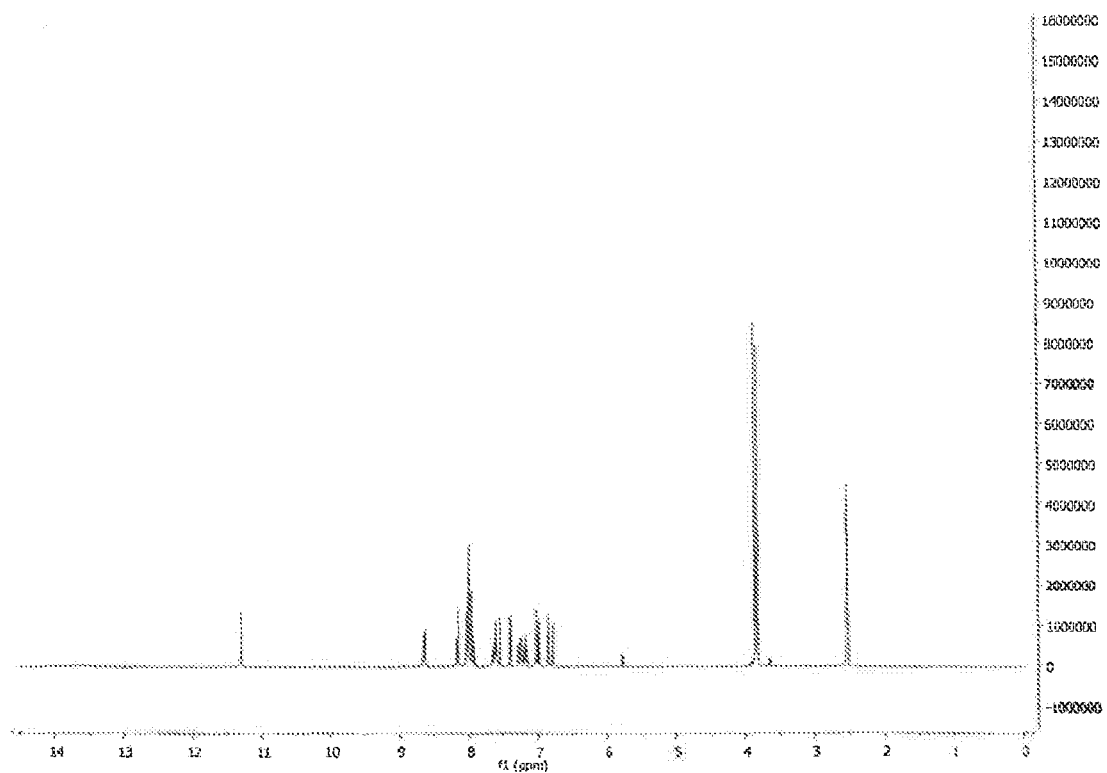
FIG. 11 shows the NMR spectrum of 1:1 tranilast saccharin cocrystal.

The $^1$H NMR spectrum of the 1:1 tranilast saccharin cocrystal, shown in FIG. 11, displays the following peaks: $^1$H NMR (400 MHz, d6-DMSO) δ: 11.29 (1H), 8.64 (1H), 8.17 (1H), 7.90-8.03 (4H), 7.61 (2H), 7.40 (1H), 7.26 (1H), 7.18 (1H), 7.01 (1H), 6.81 (1H), 3.84 (3H) and 3.81 (3 H). The peak at 8.17 ppm in the $^1$H NMR spectrum corresponds to one proton on the aromatic ring of saccharin. Comparison of the integration of this peak with that at 8.64 ppm, which corresponds to one of the aromatic protons of tranilast, indicates that the cocrystal has an API:coformer stoichiometry of 1:1.

Example 3

1:1 Tranilast Gentisic Acid Cocrystal 3.1 Preparation of a 1:1 Tranilast Gentisic Acid Cocrystal The batch of the 1:1 tranilast gentisic acid cocrystal used for characterisation was prepared as follows:

Tranilast (100 mg) was placed in a glass vial, 1.5 ml of a saturated solution of gentisic acid in acetonitrile was added to the vial. The resulting yellow slurry was placed in a shaker and matured for 5 days (RT to 50° C. on an 8 hour cycle, heating to 50° C. for 4 hours and then cooling to RT for a further 4 hours). The product was then filtered under vacuum and dried under ambient conditions overnight.

3.2 XRPD Characterisation of a 1:1 Tranilast Gentisic Acid Cocrystal

Figure 12:
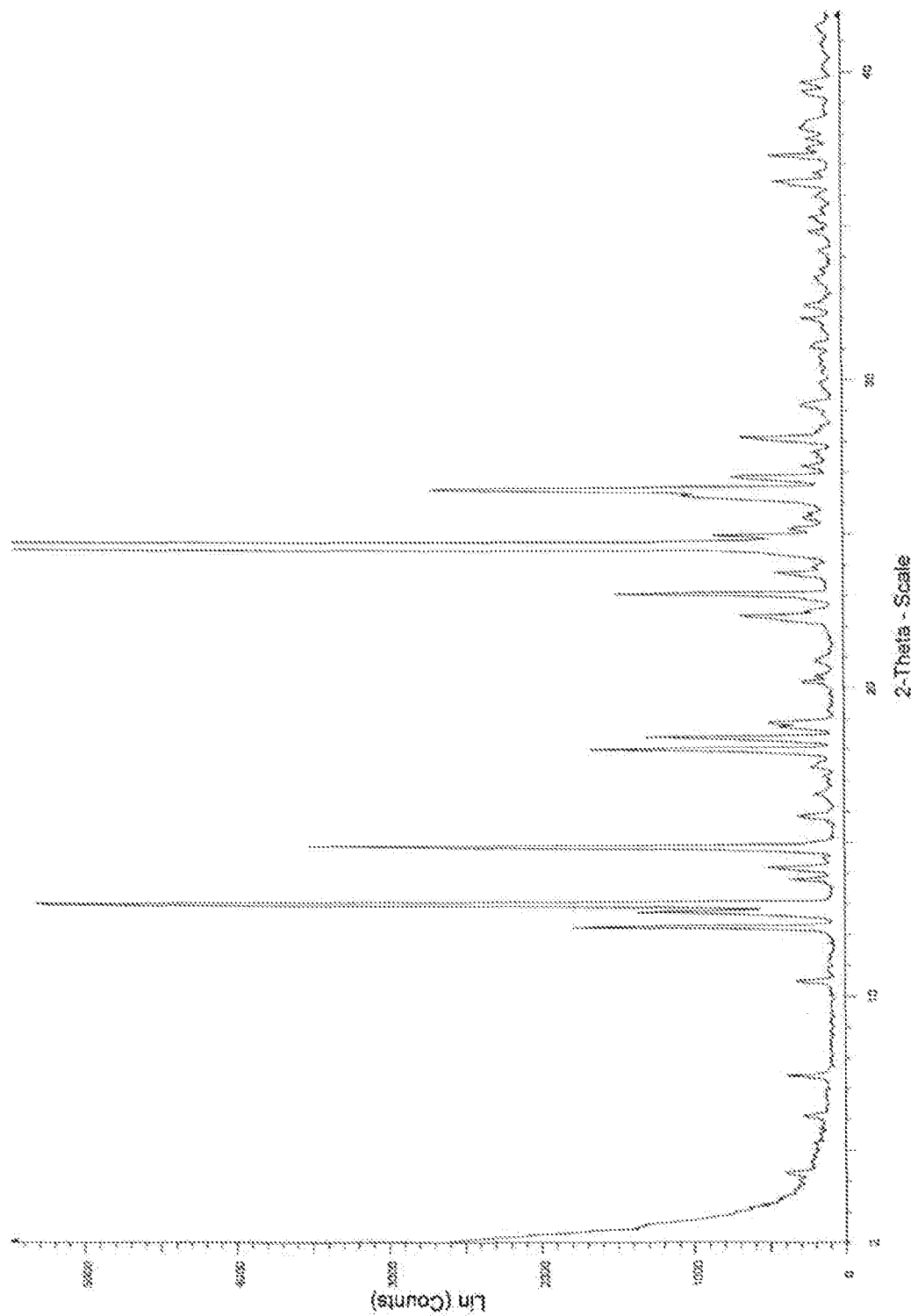
FIG. 12 shows an XRPD diagram of the 1:1 tranilast gentisic acid cocrystal.

The experimental XRPD pattern of the 1:1 tranilast gentisic acid cocrystal is shown in FIG. 12. Table 5 lists the angles, °2θ±0.2°2θ, and d-spacing of the peaks identified in the experimental XRPD pattern of FIG. 12. The entire list of peaks, or a subset thereof, may be sufficient to characterize the cocrystal, as well as by an XRPD pattern substantially similar to FIG. 12. For example, 1:1 tranilast gentisic acid cocrystal of the invention may be characterised by a powder X-ray diffraction pattern having at least three peaks selected from 7.4, 10.5, 12.2, 14.8, 15.7, and 26.4°2θ±0.2°2θ.

TABLE 5

| Angle °2θ ± 0.2 °2θ | d value Angstrom | Intensity % |
|---|---|---|
| 4.2 | 20.85 | 1.0 |
| 6.1 | 14.48 | 0.7 |
| 7.4 | 12.00 | 1.0 |
| 10.5 | 8.43 | 0.8 |
| 12.2 | 7.23 | 4.7 |
| 12.7 | 6.99 | 3.6 |
| 13.0 | 6.82 | 14.1 |
| 13.8 | 6.43 | 0.9 |
| 14.1 | 6.26 | 1.3 |
| 14.8 | 5.96 | 9.3 |
| 15.8 | 5.60 | 0.8 |
| 17.4 | 5.08 | 0.6 |
| 18.0 | 4.93 | 4.4 |
| 18.3 | 4.84 | 3.4 |
| 18.9 | 4.70 | 1.3 |
| 20.2 | 4.38 | 0.7 |
| 22.3 | 3.98 | 1.8 |
| 23.0 | 3.86 | 3.9 |
| 23.7 | 3.75 | 1.2 |
| 24.6 | 3.61 | 100.0 |
| 25.0 | 3.56 | 2.2 |
| 25.2 | 3.53 | 0.9 |
| 25.5 | 3.48 | 0.7 |
| 26.2 | 3.40 | 2.8 |
| 26.4 | 3.37 | 7.2 |
| 26.8 | 3.32 | 1.9 |
| 27.2 | 3.28 | 0.7 |
| 28.1 | 3.17 | 1.7 |
| 29.2 | 3.05 | 0.7 |
| 32.0 | 2.80 | 0.7 |
| 32.4 | 2.76 | 0.6 |
| 34.9 | 2.57 | 0.6 |
| 36.5 | 2.46 | 1.1 |
| 37.3 | 2.41 | 1.2 |
| 37.9 | 2.37 | 0.6 |
| 38.2 | 2.35 | 0.7 |
| 39.4 | 2.28 | 0.6 |
| 39.7 | 2.27 | 0.7 |

3.3 DSC of the 1:1 Tranilast Gentisic Acid Cocrystal

Figure 13:
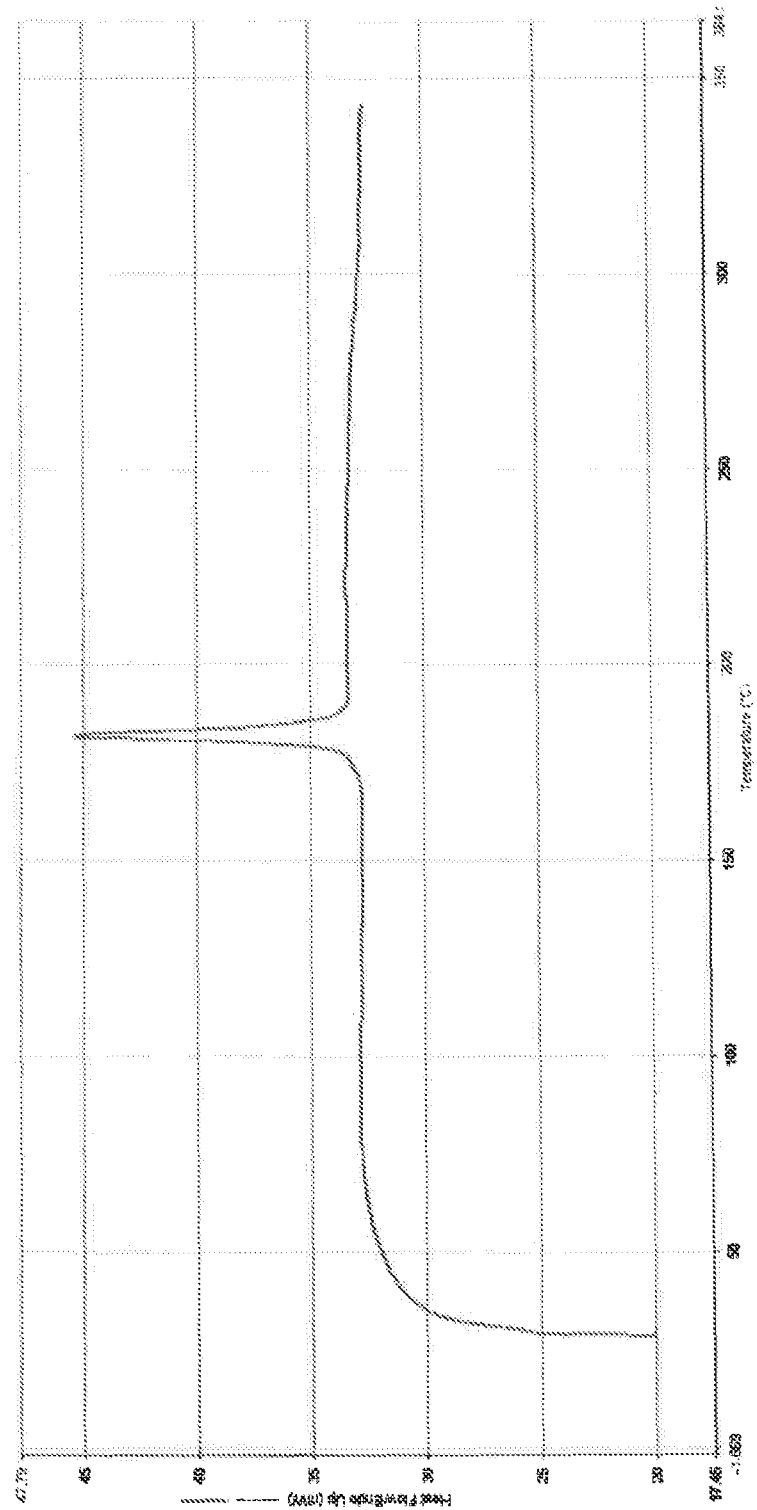
FIG. 13 shows a DSC trace for the 1:1 tranilast gentisic acid cocrystal.

The differential scanning calorimetry (DSC) trace, FIG. 13, shows a single endotherm with an onset temperature of 170.6° C. and a peak maximum of 182.1° C. corresponding to the melt of the cocrystal.

3.4 TGA of the 1:1 Tranilast Gentisic Acid Cocrystal

Figure 14:
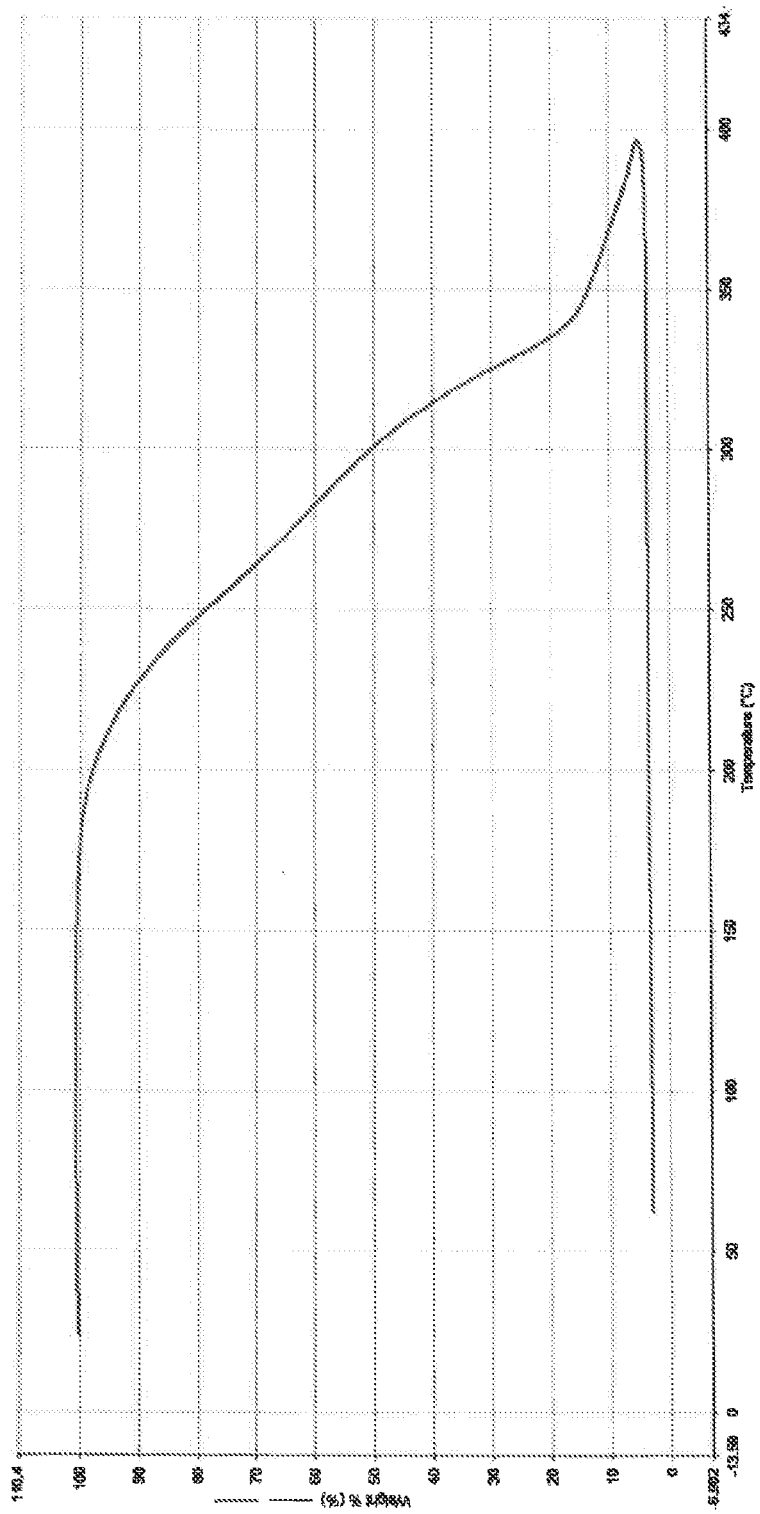
FIG. 14 shows a TGA trace for the 1:1 tranilast gentisic acid cocrystal.

The thermal gravimetric analysis (TGA) trace, FIG. 14, shows no significant weight loss prior to the cocrystal melt temperature with 99.7% weight remaining at 182° C.

3.5 $^1$H NMR Spectrum of the 1:1 Tranilast Gentisic Acid Cocrystal

Figure 15:
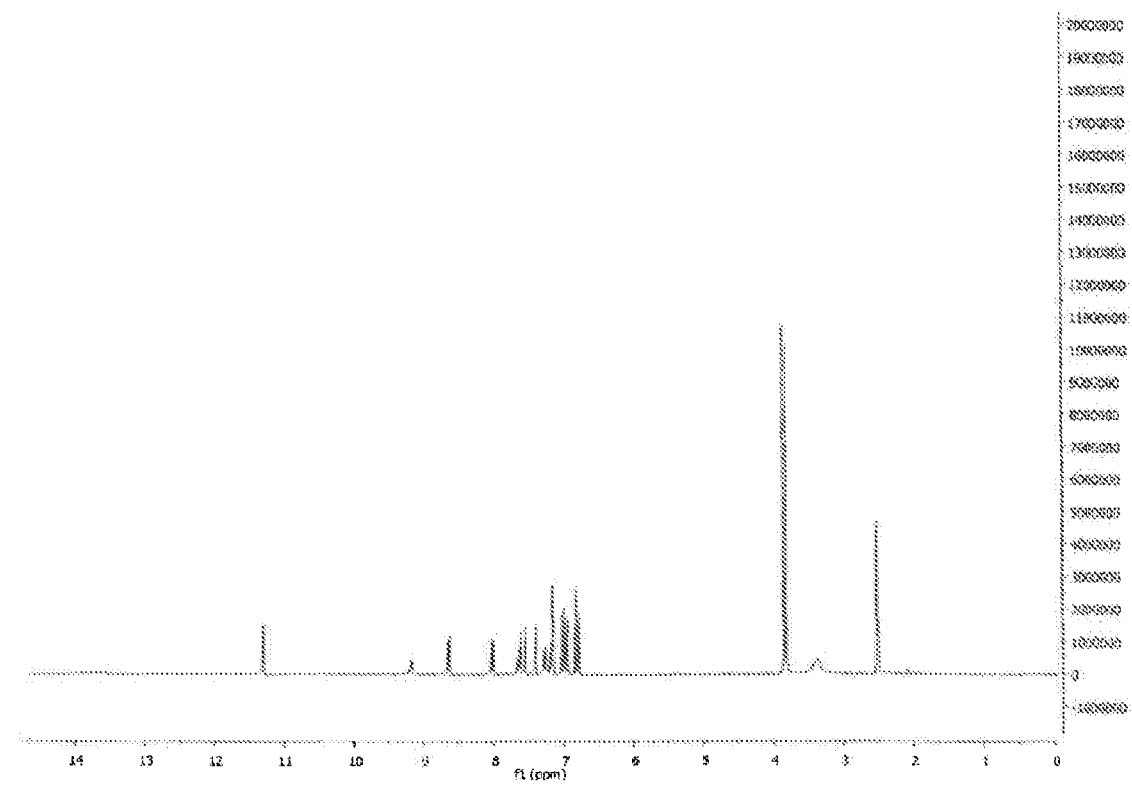
FIG. 15 shows the $^1$H NMR spectrum of 1:1 tranilast gentisic acid cocrystal.

The $^1$H NMR spectrum of the 1:1 tranilast gentisic acid cocrystal, shown in FIG. 15, displays the following peaks: $^1$H NMR (400 MHz, d6-DMSO) δ: 11.30 (1H), 8.65 (1H), 8.02 (1H), 7.55-7.66 (2H), 7.40 (1H), 7.26 (1H), 7.15-7.21 (2H), 6.94-7.02 (2H), 6.77-6.84 (2H), 3.84 (3H) and 3.81 (3H). The multiplet between 6.94 and 7.02 ppm which integrates for 2 protons, corresponds to one of the aromatic protons of tranilast and one of the aromatic protons of gentisic acid. This indicates that the cocrystal has an API:coformer stoichiometry of 1:1.

Example 4

1:1 Tranilast Salicylic Acid Cocrystal 4.1 Preparation of a 1:1 Tranilast Gentisic Acid Cocrystal The batch of the 1:1 tranilast salicyclic acid cocrystal used for characterisation was prepared as follows:

Tranilast (250 mg) and salicylic acid (104 mg) were weighed into a glass vial. Dichloromethane (2.0 ml) was added to the vial. The resulting yellow slurry was placed in a shaker and matured for 5 days (RT to 50° C. on an 8 hour cycle, heating to 50° C. for 4 hours and then cooling to RT for a further 4 hours). The product was then filtered under vacuum dried under ambient conditions overnight.

4.2 XRPD Characterisation of a 1:1 Tranilast Salicylic Acid Cocrystal

Figure 16:
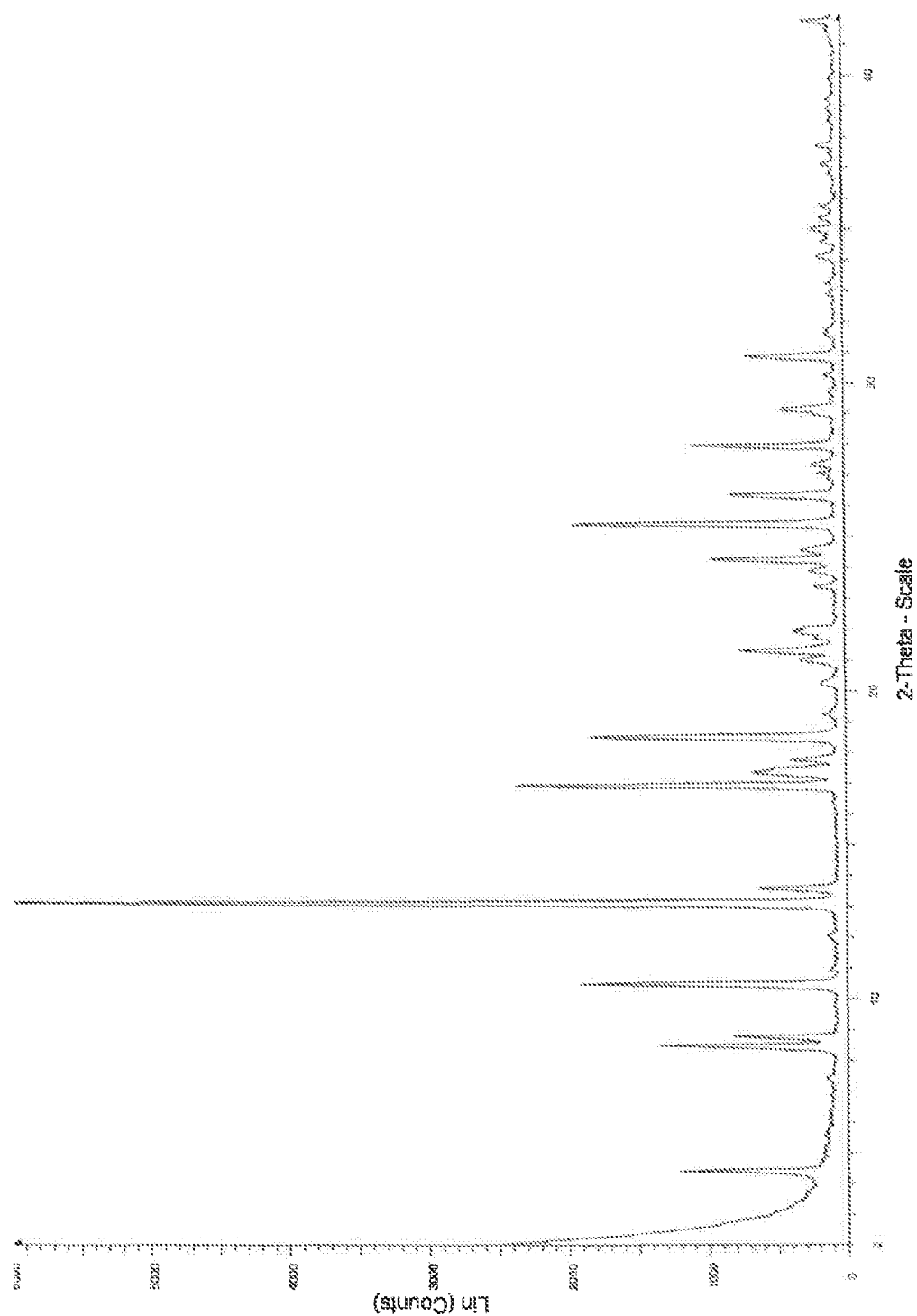
FIG. 16 shows an XRPD diagram of the 1:1 tranilast salicylic acid cocrystal.

The experimental XRPD pattern of the 1:1 tranilast salicylic acid cocrystal is shown in FIG. 16. Table 6 lists the angles, °2θ±0.2°2θ, and d-spacing of the peaks identified in the experimental XRPD pattern of FIG. 15. The entire list of peaks, or a subset thereof, may be sufficient to characterize the cocrystal, as well as by an XRPD pattern substantially similar to FIG. 16. For example, a 1:1 tranilast salicylic acid cocrystal of the invention may be characterised by a powder X-ray diffraction pattern having at least three peaks selected from 4.4, 10.4, 13.1, 16.9 and 18.5 °2θ±0.2°2θ.

TABLE 6

| Angle °2θ ± 0.2 °2θ | d value Angstrom | Intensity % |
|---|---|---|
| 4.4 | 20.24 | 18.7 |
| 8.4 | 10.53 | 21.1 |
| 8.7 | 10.10 | 12.7 |
| 10.4 | 8.47 | 29.8 |
| 13.1 | 6.77 | 100.0 |
| 13.6 | 6.51 | 9.8 |
| 16.9 | 5.24 | 37.0 |
| 17.3 | 5.12 | 10.3 |
| 17.8 | 4.98 | 5.9 |
| 18.5 | 4.80 | 28.8 |
| 21.0 | 4.23 | 4.8 |
| 21.3 | 4.17 | 11.7 |
| 21.9 | 4.05 | 5.6 |
| 23.4 | 3.80 | 3.4 |
| 23.9 | 3.72 | 3.7 |
| 24.3 | 3.66 | 14.8 |
| 24.6 | 3.62 | 4.7 |
| 25.4 | 3.50 | 30.8 |
| 26.4 | 3.38 | 12.5 |
| 27.3 | 3.26 | 3.5 |
| 28.0 | 3.19 | 17.0 |
| 29.1 | 3.06 | 6.8 |

TABLE 6-continued

| Angle °2θ ± 0.2 °2θ | d value Angstrom | Intensity % |
|---|---|---|
| 30.9 | 2.90 | 10.9 |
| 35.0 | 2.56 | 3.4 |
| 41.8 | 2.16 | 4.1 |

4.3 DSC of the 1:1 Tranilast Salicylic Acid Cocrystal

Figure 17:
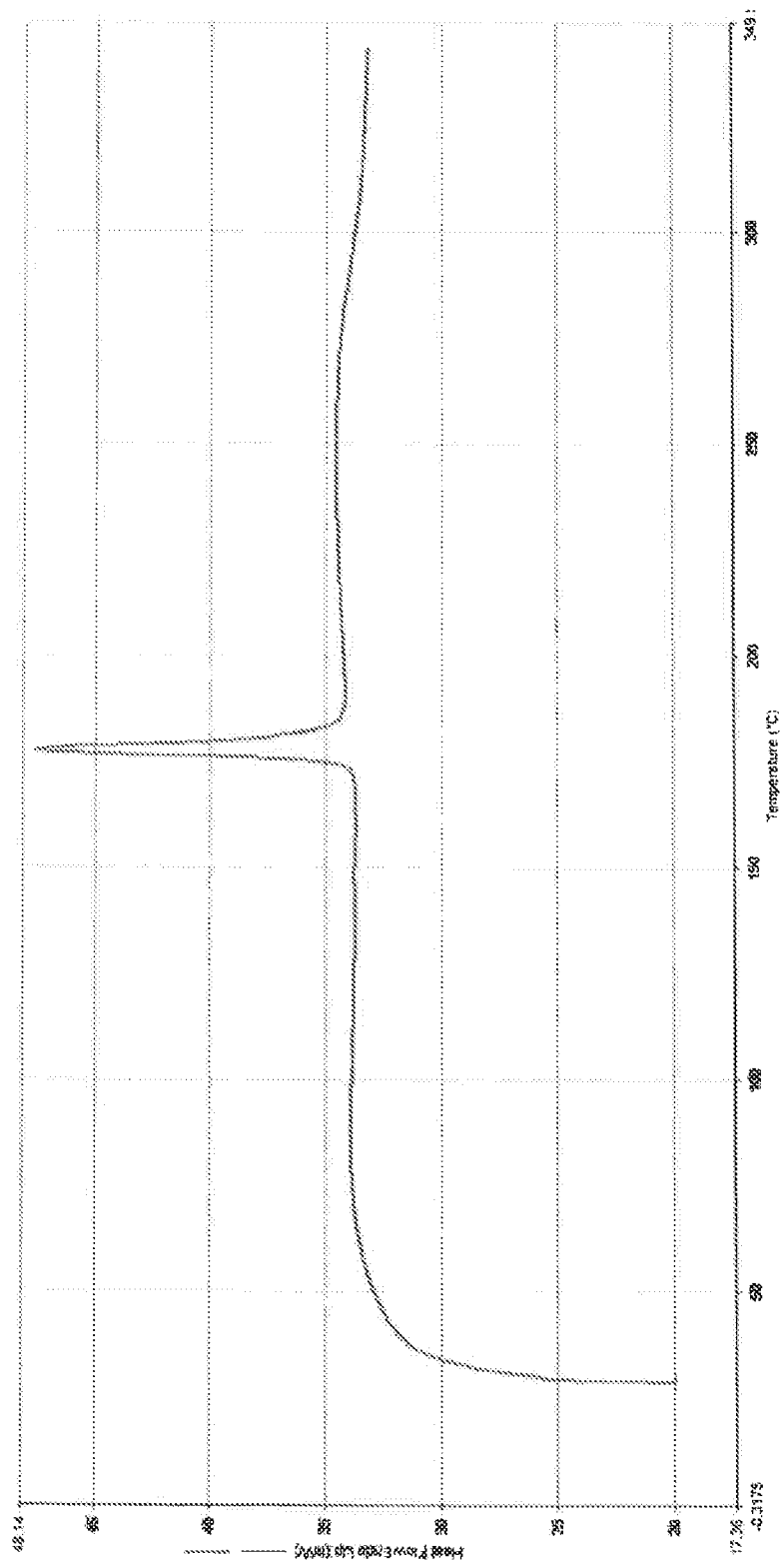
FIG. 17 shows a DSC trace for the 1:1 tranilast salicylic acid cocrystal.

The differential scanning calorimetry (DSC) trace, FIG. 17, shows a single endotherm with an onset temperature of 170.6° C. and a peak maximum of 177.7° C.

4.4 TGA of the 1:1 Tranilast Salicylic Acid Cocrystal

Figure 18:
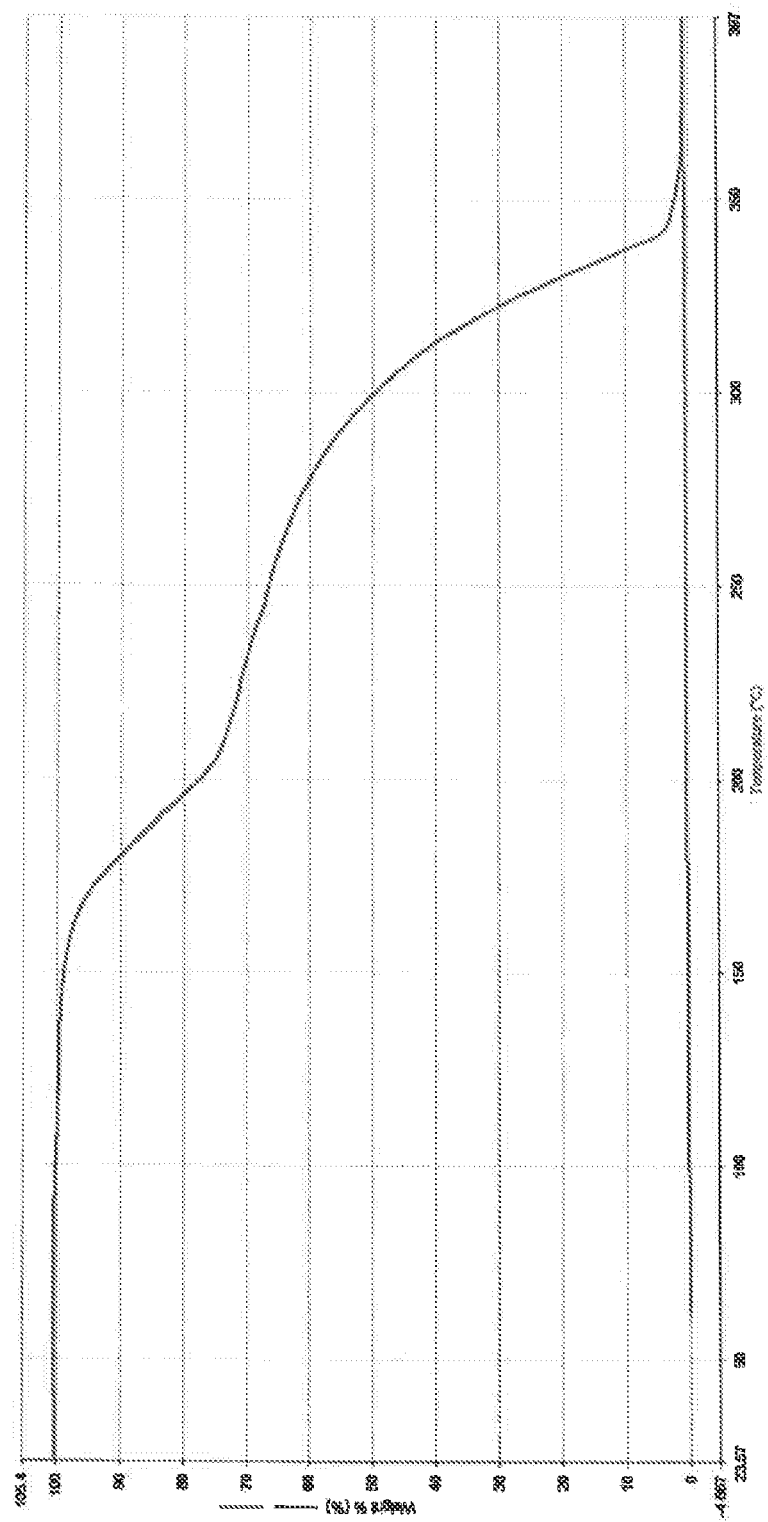
FIG. 18 shows a TGA trace for the 1:1 tranilast salicylic acid cocrystal.

The thermal gravimetric analysis (TGA) trace is shown in FIG. 18. It can be seen that the cocrystal begins to lose weight at 141° C.

4.5 $^1$H NMR Spectrum of the 1:1 Tranilast Salicylic Acid Cocrystal

Figure 19:
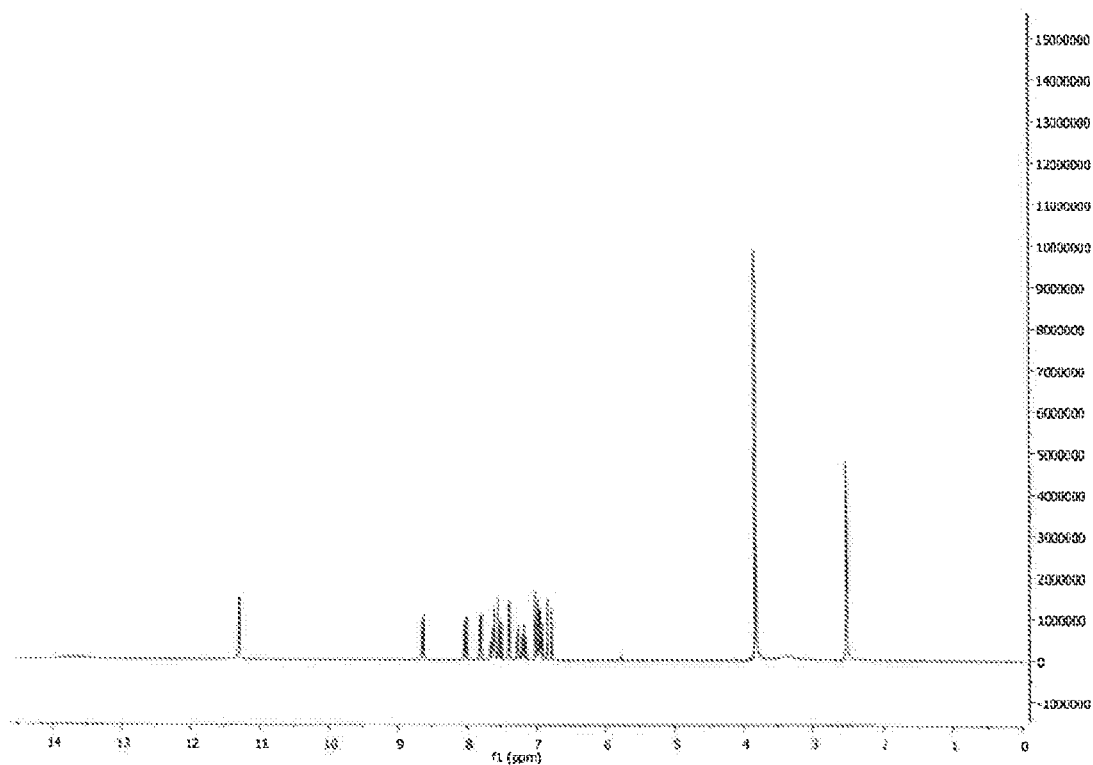
FIG. 19 shows the $^1$H NMR spectrum of 1:1 tranilast salicylic acid cocrystal.

The $^1$H NMR spectrum of the 1:1 tranilast salicylic acid cocrystal, shown in FIG. 19, displays the following peaks: $^1$H NMR (400 MHz, d6-DMSO) δ: 11.30 (1H), 8.64 (1H), 8.02 (1H), 7.80 (1H), 7.49-7.66 (3H), 7.40 (1H), 7.26 (1H), 7.18 (1H), 6.90-7.02 (3H), 6.82 (1H), 3.84 (3H) and 3.81 (3H). The peak at 7.80 ppm in the $^1$H NMR spectrum corresponds to one proton on the aromatic ring of salicylic acid. Comparison of the integration of this peak with that at 8.64 ppm, which corresponds to one of the aromatic protons of tranilast, indicates that the cocrystal has an API:coformer stoichiometry of 1:1.

Example 5

1:1 Tranilast Urea Cocrystal 5.1 Preparation of a 1:1 Tranilast Urea Cocrystal

The batch of the 1:1 tranilast urea cocrystal used for characterisation was prepared as follows:

Tranilast (100 mg) and urea (18.3 mg) were placed in were placed in a stainless steel ball mill. Isopropyl acetate (2 drops) was added. The two components were ground together for 60 minute at 20 Hz. The product was removed from the mill and the resulting colourless powder was left to dry under ambient temperatures overnight.

5.2 XRPD Characterisation of a 1:1 Tranilast Urea Cocrystal

Figure 20:
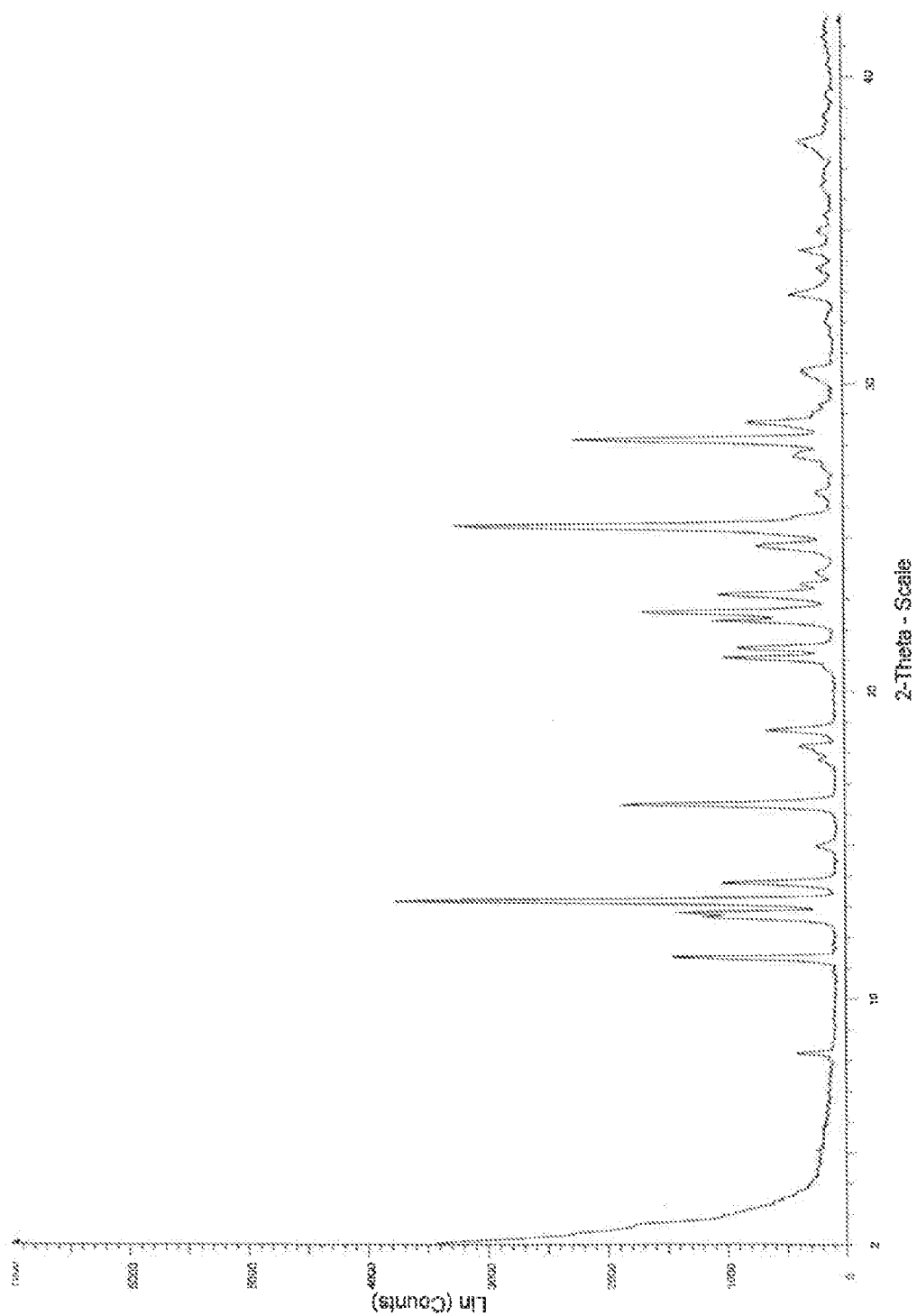
FIG. 20 shows an XRPD diagram of the 1:1 tranilast urea cocrystal.

The experimental XRPD pattern of the 1:1 tranilast gentisic acid cocrystal is shown in FIG. 20. Table 7 lists the angles, °2θ±0.2°2θ, and d-spacing of the peaks identified in the experimental XRPD pattern of FIG. 20. The entire list of peaks, or a subset thereof, may be sufficient to characterize the cocrystal, as well as by an XRPD pattern substantially similar to FIG. 20. For example, a 1:1 tranilast urea cocrystal of the invention may be characterised by a powder X-ray diffraction pattern having at least three peaks selected from 8.2, 11.3, 13.8, 15.0, 16.3 and 25.3 °2θ±0.2°2θ.

TABLE 7

| Angle °2θ ± 0.2 °2θ | d value Angstrom | Intensity % |
|---|---|---|
| 8.2 | 10.76 | 10.8 |
| 11.3 | 7.81 | 38.2 |
| 12.6 | 7.00 | 33.0 |
| 12.8 | 6.93 | 37.2 |
| 13.2 | 6.71 | 100.0 |
| 13.8 | 6.42 | 27.2 |
| 15.0 | 5.91 | 6.3 |

TABLE 7-continued

| Angle °2θ ± 0.2 °2θ | d value Angstrom | Intensity % |
|---|---|---|
| 16.3 | 5.43 | 49.5 |
| 17.7 | 5.00 | 5.8 |
| 18.2 | 4.86 | 9.9 |
| 18.7 | 4.73 | 17.0 |
| 21.1 | 4.21 | 26.7 |
| 21.4 | 4.14 | 23.2 |
| 22.3 | 3.99 | 28.7 |
| 22.5 | 3.94 | 45.1 |
| 23.1 | 3.84 | 27.5 |
| 23.5 | 3.79 | 9.1 |
| 23.8 | 3.73 | 6.1 |
| 24.7 | 3.60 | 19.1 |
| 25.3 | 3.51 | 86.6 |
| 26.4 | 3.37 | 6.1 |
| 27.7 | 3.22 | 10.8 |
| 28.2 | 3.17 | 59.8 |
| 28.8 | 3.10 | 21.0 |
| 30.5 | 2.93 | 9.0 |
| 33.0 | 2.72 | 11.5 |
| 34.4 | 2.61 | 9.1 |
| 38.0 | 2.37 | 9.2 |

5.3 DSC of the 1:1 Tranilast Urea Cocrystal

Figure 21:
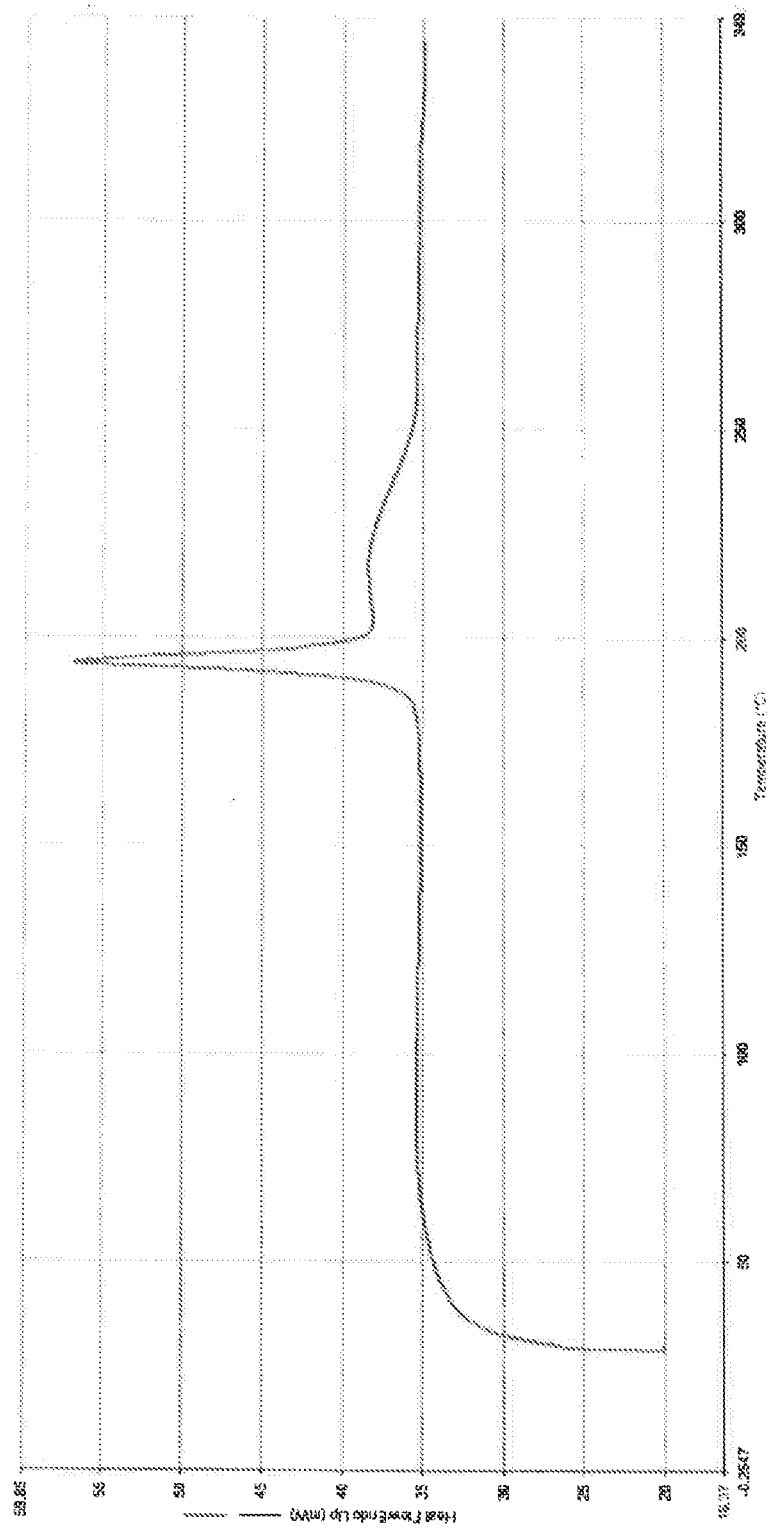
FIG. 21 shows a DSC trace for the 1:1 tranilast urea cocrystal.

The differential scanning calorimetry (DSC) trace, FIG. 21, shows a sharp endotherm with an onset temperature of 176.5° C. and a peak maximum of 193.9° C. followed by a broad endothermic event between 202 and 254° C.

5.4 TGA of the 1:1 Tranilast Urea Cocrystal

Figure 22:
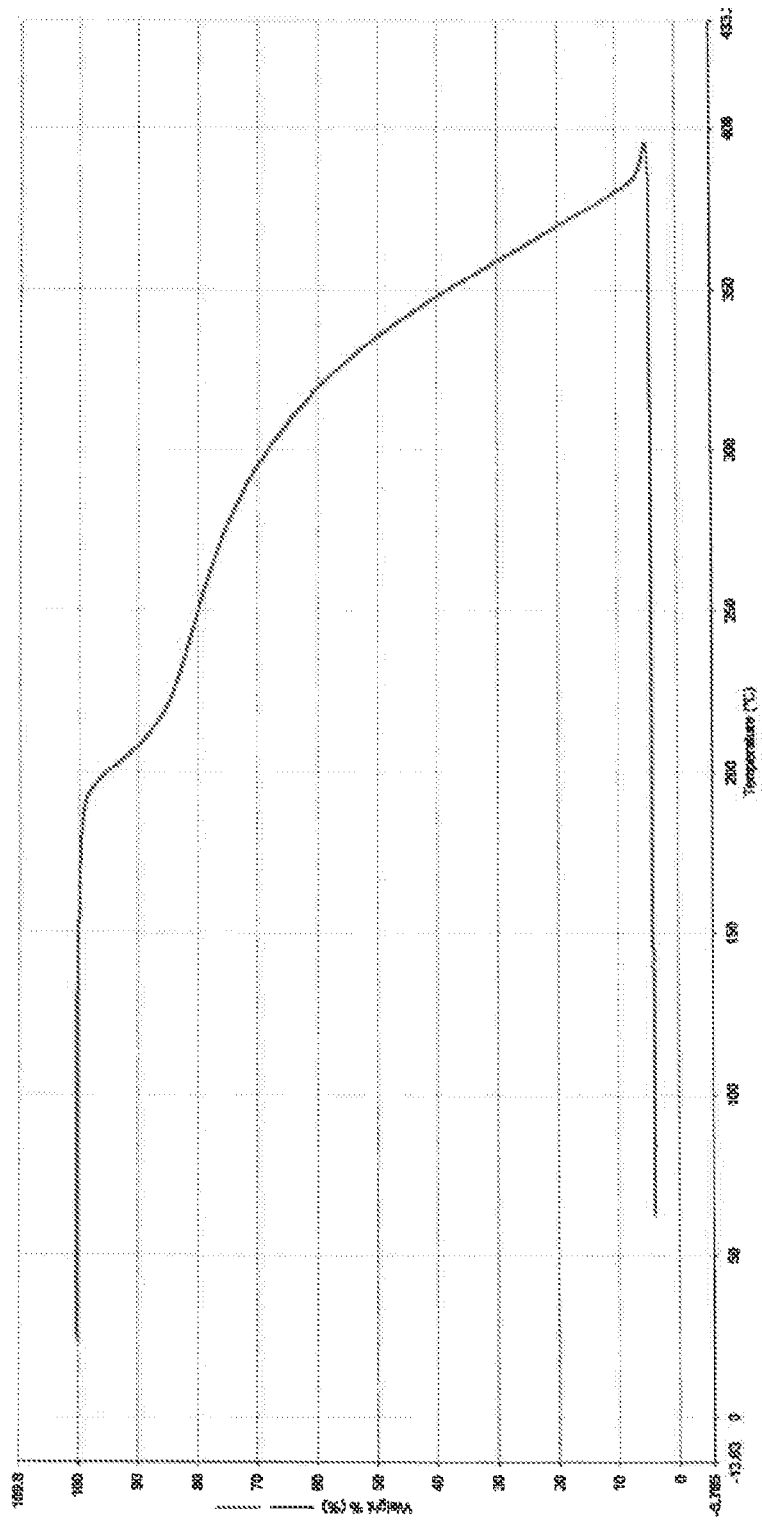
FIG. 22 shows a TGA trace for the 1:1 tranilast urea cocrystal.

The thermal gravimetric analysis (TGA) trace, FIG. 22, shows no significant weight loss prior to 176.5° C., with 99.5% weight remaining at this temperature. The TGA shows that there is a weight loss of 15.5% between 177 and 223° C. This corresponds to one molar equivalent of urea.

5.5 $^1$H NMR Spectrum of the 1:1 Tranilast Urea Cocrystal

Figure 23:
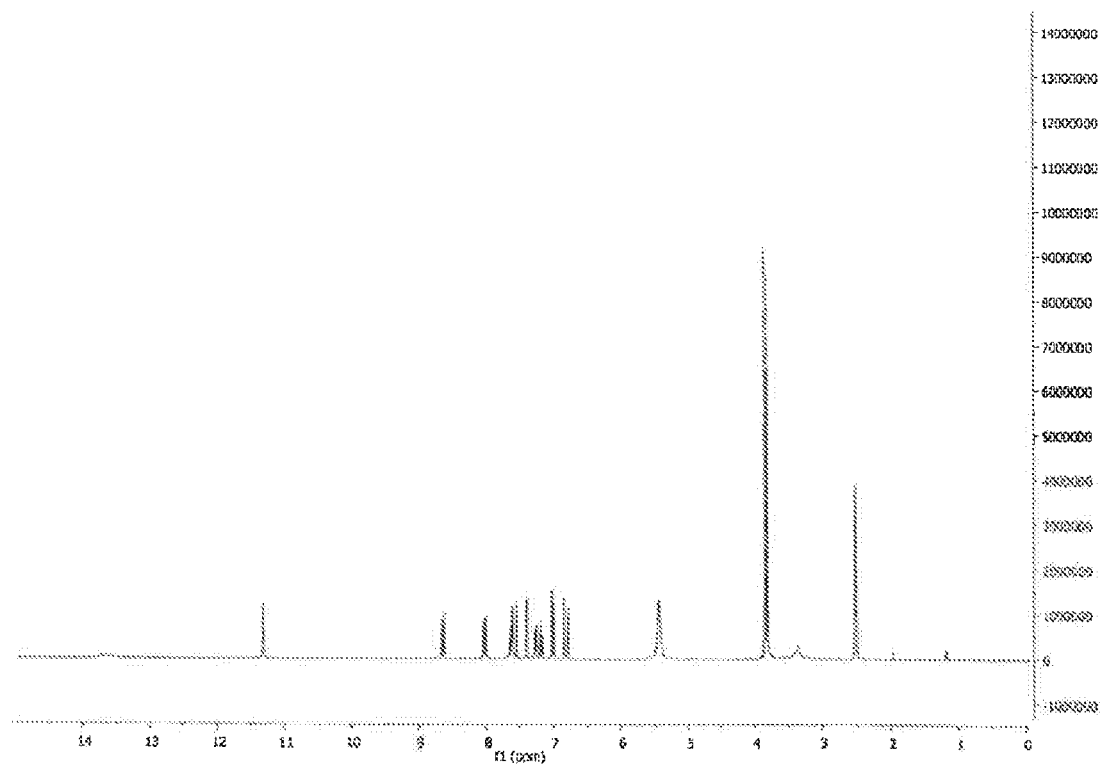
FIG. 23 shows the $^1$H NMR spectrum of 1:1 tranilast urea cocrystal.

The $^1$H NMR spectrum of the 1:1 tranilast urea cocrystal, shown in FIG. 23, displays the following peaks: $^1$H NMR (400 MHz, d6-DMSO) δ: 13.64 (1H), 11.32 (1H), 8.64 (1H), 8.02 (1H), 7.55-7.66 (2H), 7.40 (1H), 7.27 (1H), 7.17 (1H), 7.01 (1H), 6.82 (1H), 5.84 (4H), 3.84 (3H) and 3.81 (3H). The peak at 5.84 ppm in the $^1$H NMR spectrum corresponds to the four protons of urea. Comparison of the integration of this peak with that at 8.64 ppm, which corresponds to one of the aromatic protons of tranilast, indicates that the cocrystal has an API:coformer stoichiometry of 1:1.

Example 6

1:1 Tranilast 4-Aminobenzoic Acid Cocrystal 6.1 Preparation of a 1:1 Tranilast 4-Aminobenzoic Acid Cocrystal The batch of the 1:1 tranilast 4-aminobenzoic acid cocrystal used for characterisation was prepared as follows:

Tranilast (300 mg) and was weighed into a glass vial. 3 ml of a saturated solution of 4-aminobenzoic acid in isopropylacetate was added to the vial. The resulting yellow slurry was placed in a shaker and matured for days (RT to 50° C. on an 8 hour cycle, heating to 50° C. for 4 hours and then cooling to RT for a further 4 hours). The product was then filtered under vacuum and the resulting colourless crystals were dried under ambient conditions overnight.

6.2 XRPD Characterisation of a 1:1 Tranilast 4-Aminobenzoic Acid Cocrystal

Figure 24:
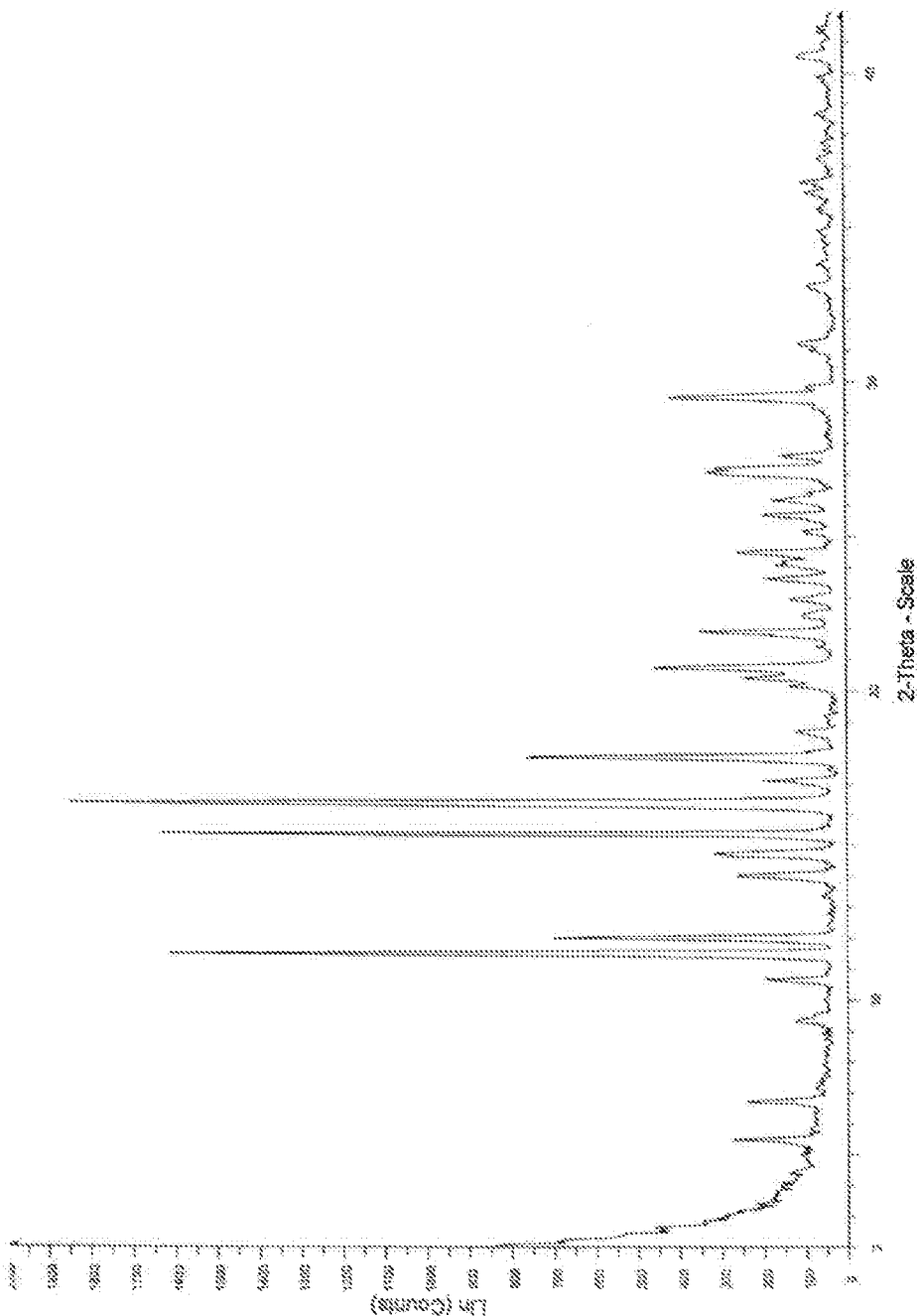
FIG. 24 shows an XRPD diagram of the 1:1 tranilast 4-aminobenzoic acid cocrystal.

The experimental XRPD pattern of the 1:1 tranilast 4-aminobenzoic acid cocrystal is shown in FIG. 24. Table 8 lists the angles, °2θ±0.2°θ, and d-spacing of the peaks identified in the experimental XRPD pattern of FIG. 24. The entire list of peaks, or a subset thereof, may be sufficient to characterize the cocrystal, as well as by an XRPD pattern substantially similar to FIG. 24. For example, a 1:1 tranilast 4-aminobenzoic acid cocrystal of the invention may be characterised by a powder X-ray diffraction pattern having at least three peaks selected from 5.4, 6.7, 11.5, 12.0, 16.4 and 17.9 °2θ±0.2θ.

TABLE 8

| Angle °2θ ± 0.2 °2θ | d value Angstrom | Intensity % |
|---|---|---|
| 5.4 | 16.21 | 14.8 |
| 6.7 | 13.23 | 12.9 |
| 9.3 | 9.51 | 6.7 |
| 10.6 | 8.34 | 10.5 |
| 11.5 | 7.71 | 87.3 |
| 12.0 | 7.37 | 37.7 |
| 14.0 | 6.30 | 13.9 |
| 14.7 | 6.02 | 16.9 |
| 15.4 | 5.77 | 88.4 |
| 16.4 | 5.41 | 100.0 |
| 17.1 | 5.19 | 10.4 |
| 17.9 | 4.96 | 41.2 |
| 18.7 | 4.75 | 6.3 |
| 20.2 | 4.39 | 7.3 |
| 20.4 | 4.35 | 13.1 |
| 20.8 | 4.27 | 24.6 |
| 21.9 | 4.05 | 18.7 |
| 22.4 | 3.96 | 5.4 |
| 22.9 | 3.87 | 6.9 |
| 23.6 | 3.76 | 10.3 |
| 24.2 | 3.68 | 8.9 |
| 24.5 | 3.64 | 13.9 |
| 25.2 | 3.54 | 5.4 |
| 25.7 | 3.46 | 10.4 |
| 26.2 | 3.40 | 9.3 |
| 27.1 | 3.28 | 17.9 |
| 27.6 | 3.23 | 8.3 |
| 29.5 | 3.03 | 22.6 |
| 29.9 | 2.99 | 5.0 |
| 31.0 | 2.88 | 4.4 |
| 31.3 | 2.86 | 5.8 |
| 33.1 | 2.70 | 4.5 |
| 36.2 | 2.48 | 4.8 |
| 36.5 | 2.46 | 5.3 |
| 40.6 | 2.22 | 5.8 |

6.3 DSC of the 1:1 Tranilast 4-Aminobenzoic Acid Cocrystal

Figure 25:
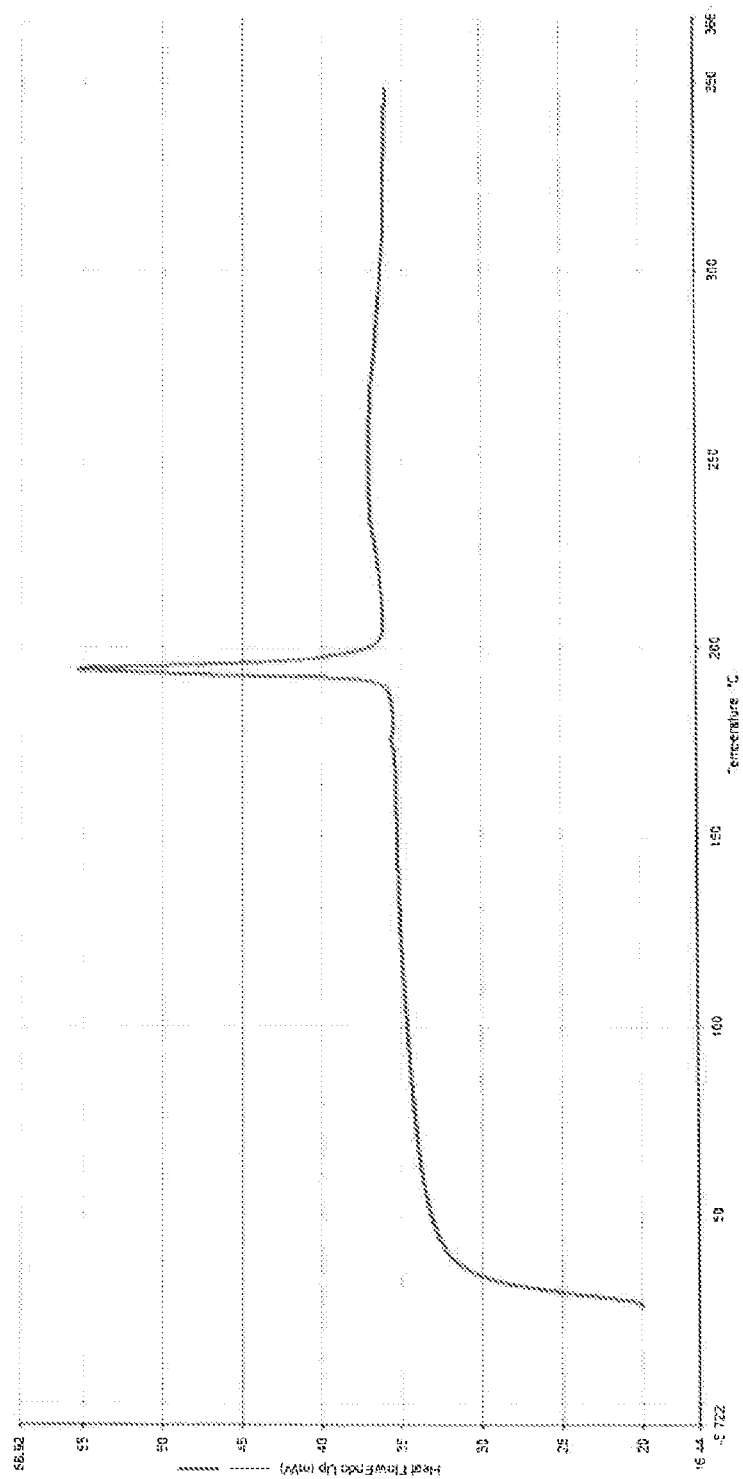
FIG. 25 shows a DSC trace for the 1:1 tranilast 4-aminobenzoic acid cocrystal.

The differential scanning calorimetry (DSC) trace, FIG. 25, shows a sharp endotherm with a peak maximum of 194.1° C. corresponding to the melt of the cocrystal.

6.4 TGA of the 1:1 Tranilast 4-Aminobenzoic Acid Cocrystal

Figure 26:
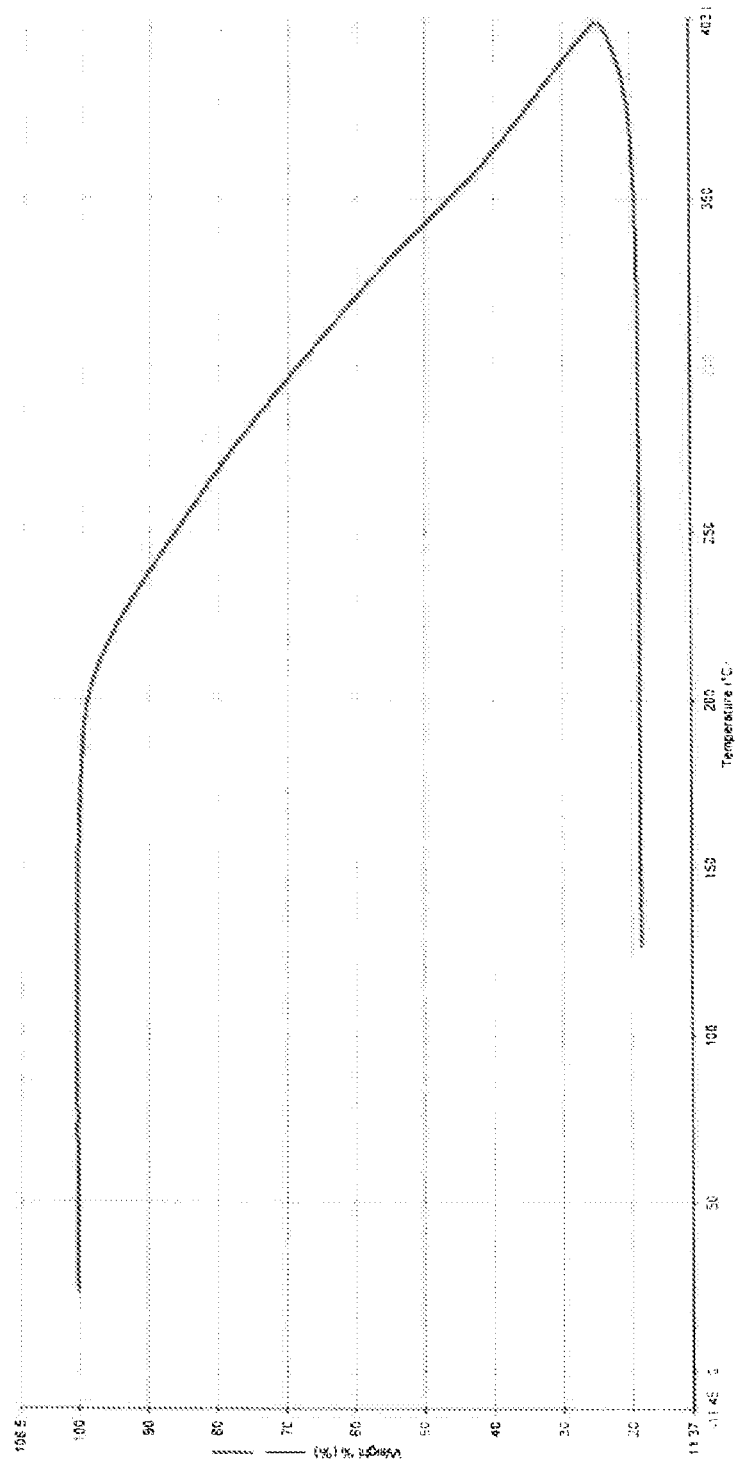
FIG. 26 shows a TGA trace for the 1:1 tranilast 4-aminobenzoic acid cocrystal.

The thermal gravimetric analysis (TGA) trace, FIG. 26, shows no significant weight loss prior to the cocrystal melt temperature, with 99.5% weight remaining at 190° C.

6.5 $^1$H NMR Spectrum of the 1:1 Tranilast 4-Aminobenzoic Cocrystal

Figure 27:
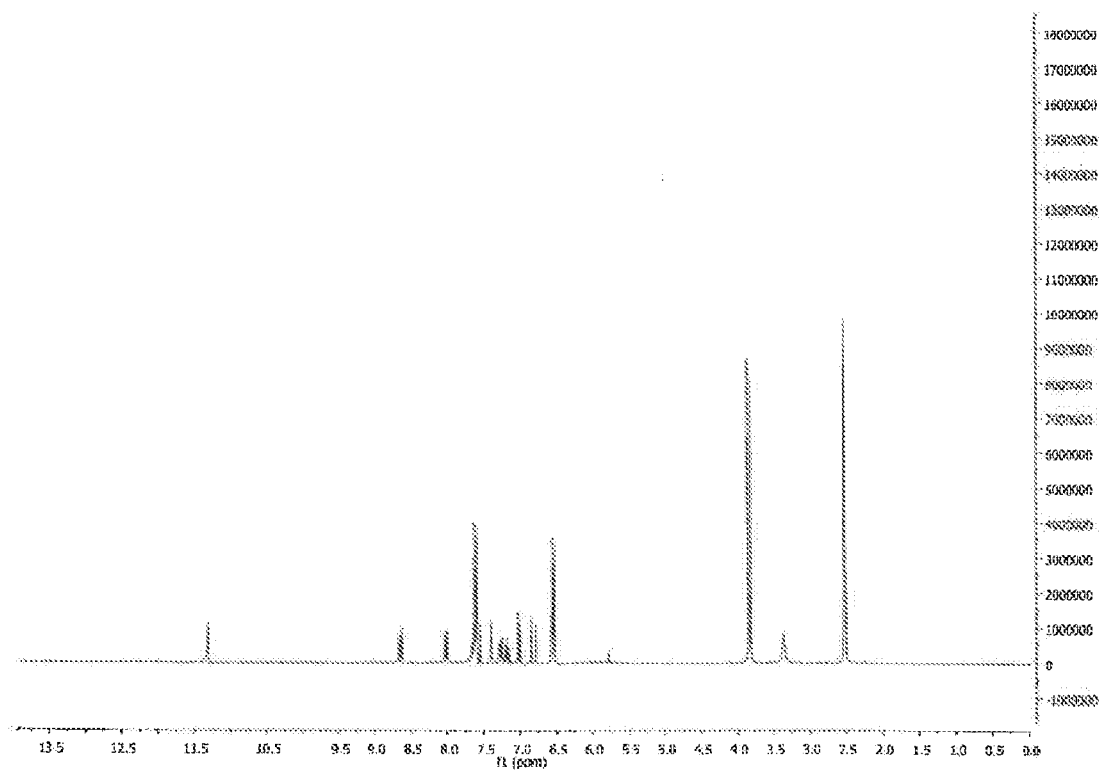
FIG. 27 shows the $^1$H NMR spectrum of 1:1 tranilast 4-aminobenzoic acid cocrystal.

The $^1$H NMR spectrum of the 1:1 tranilast 4-aminobenzoic acid cocrystal, shown in FIG. 27, displays the following peaks: $^1$H NMR (400 MHz, d6-DMSO) δ: 11.31 (1H), 8.64 (1H), 8.02 (1H), 7.55-7.66 (4H), 7.40 (1H), 7.26 (1H), 7.14 (1H), 7.01 (1H), 6.82 (1H), 6.54 (2H), 3.84 (3H) and 3.81 (3H). The peak at 6.54 ppm in the $^1$H NMR spectrum corresponds to the two protons on the aromatic ring of 4-aminobenzoic acid. Comparison of the integration of this peak with that at 8.64 ppm, which corresponds to one of the aromatic protons of tranilast, indicates that the cocrystal has an API:coformer stoichiometry of 1:1.

Example 7

1:1 Tranilast 2,4-Dihydroxybenzoic Acid Cocrystal 7.1 Preparation of a 1:1 Tranilast 2,4-Dihydroxybenzoic Acid Cocrystal Tranilast (100 mg) was weighed into a glass vial. 3 ml of a saturated solution of 2,4-dihydroxybenzoic acid in acetonitrile was added to the vial and the vial sealed. The resulting yellow slurry was placed in a shaker and matured for 5 days (RT to 50° C. on an 8 hour cycle, heating to 50° C. for 4 hours and then cooling to RT for a further 4 hours). The product was then filtered under vacuum and the resulting colourless crystals were dried under ambient conditions overnight.

Figure 28:
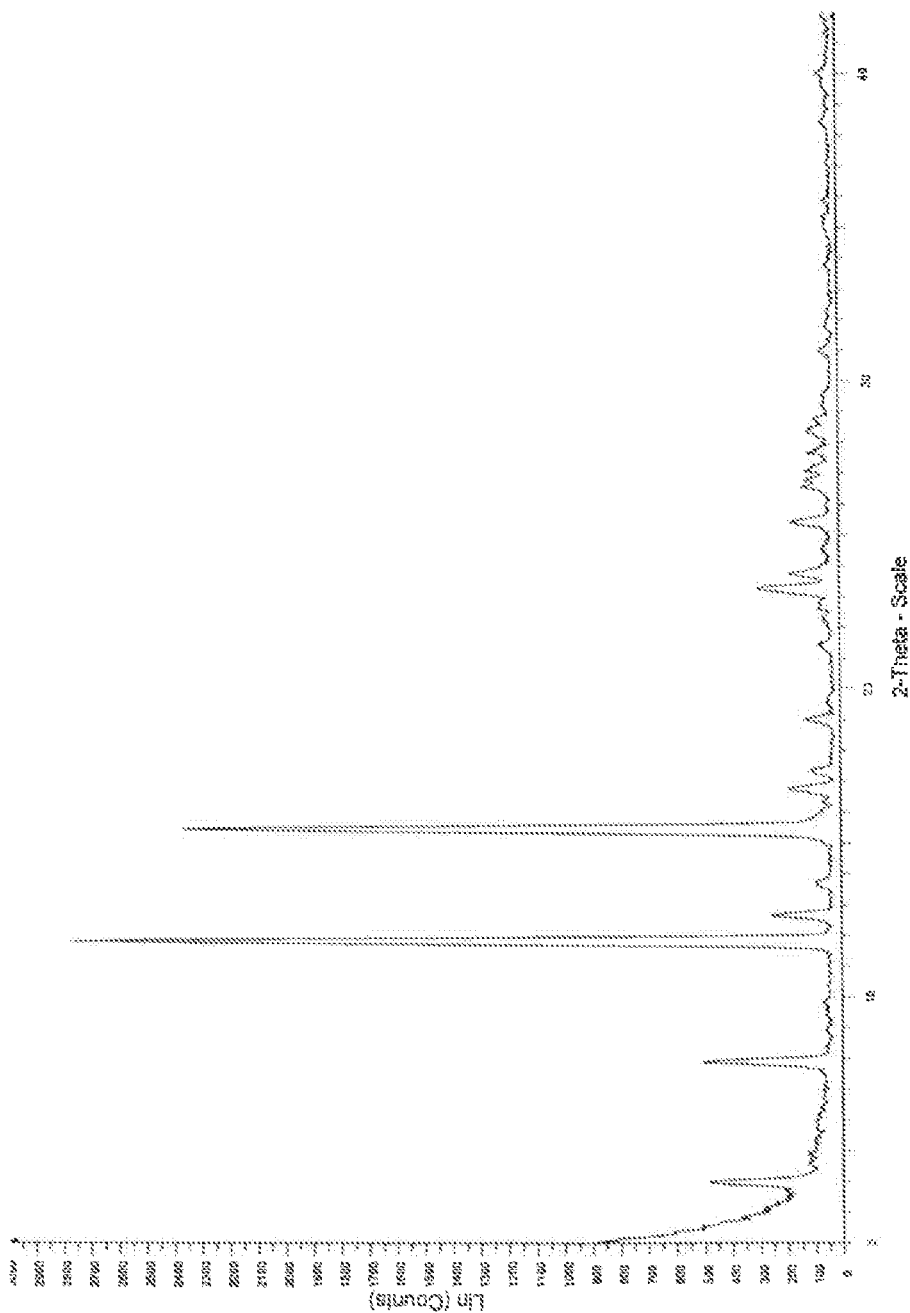
FIG. 28 shows an XRPD diagram of the 1:1 tranilast 2,4-dihydroxybenzoic acid cocrystal.

7.2 XRPD Characterisation of a 1:1 Tranilast 2,4-Dihydroxybenzoic Acid Cocrystal The experimental XRPD pattern of the 1:1 tranilast 2,4-dihydroxybenzoic acid cocrystal is shown in FIG. 28. Table 9 lists the angles, °2θ±0.2°2θ, and d-spacing of the peaks identified in the experimental XRPD pattern of FIG. 28. The entire list of peaks, or a subset thereof, may be sufficient to characterize the cocrystal, as well as by an XRPD pattern substantially similar to FIG. 28. For example, a 1:1 tranilast 2,4-dihydroxybenzoic acid cocrystal of the invention may be characterised by a powder X-ray diffraction pattern having at least three peaks selected from 3.9, 7.9, 11.8, 12.6 and 15.4 °2θ±0.2°2θ.

TABLE 9

| Angle °2θ ± 0.2 °2θ | d value Angstrom | Intensity % |
|---|---|---|
| 3.9 | 22.45 | 17.3 |
| 7.9 | 11.20 | 18.1 |
| 11.8 | 7.49 | 100.0 |
| 12.6 | 7.00 | 9.0 |
| 13.7 | 6.48 | 3.1 |
| 15.4 | 5.73 | 85.4 |
| 16.8 | 5.29 | 6.8 |
| 17.3 | 5.12 | 3.6 |
| 19.0 | 4.67 | 4.6 |
| 21.4 | 4.15 | 2.8 |
| 22.6 | 3.92 | 2.7 |
| 23.3 | 3.82 | 10.5 |
| 23.7 | 3.74 | 6.4 |
| 25.4 | 3.50 | 6.2 |
| 26.5 | 3.36 | 4.7 |
| 27.1 | 3.29 | 4.2 |
| 27.7 | 3.21 | 4.0 |
| 28.4 | 3.14 | 3.9 |
| 28.8 | 3.10 | 3.3 |

7.3 DSC of the 1:1 Tranilast 2,4-Dihydroxybenzoic Acid Cocrystal

Figure 29:
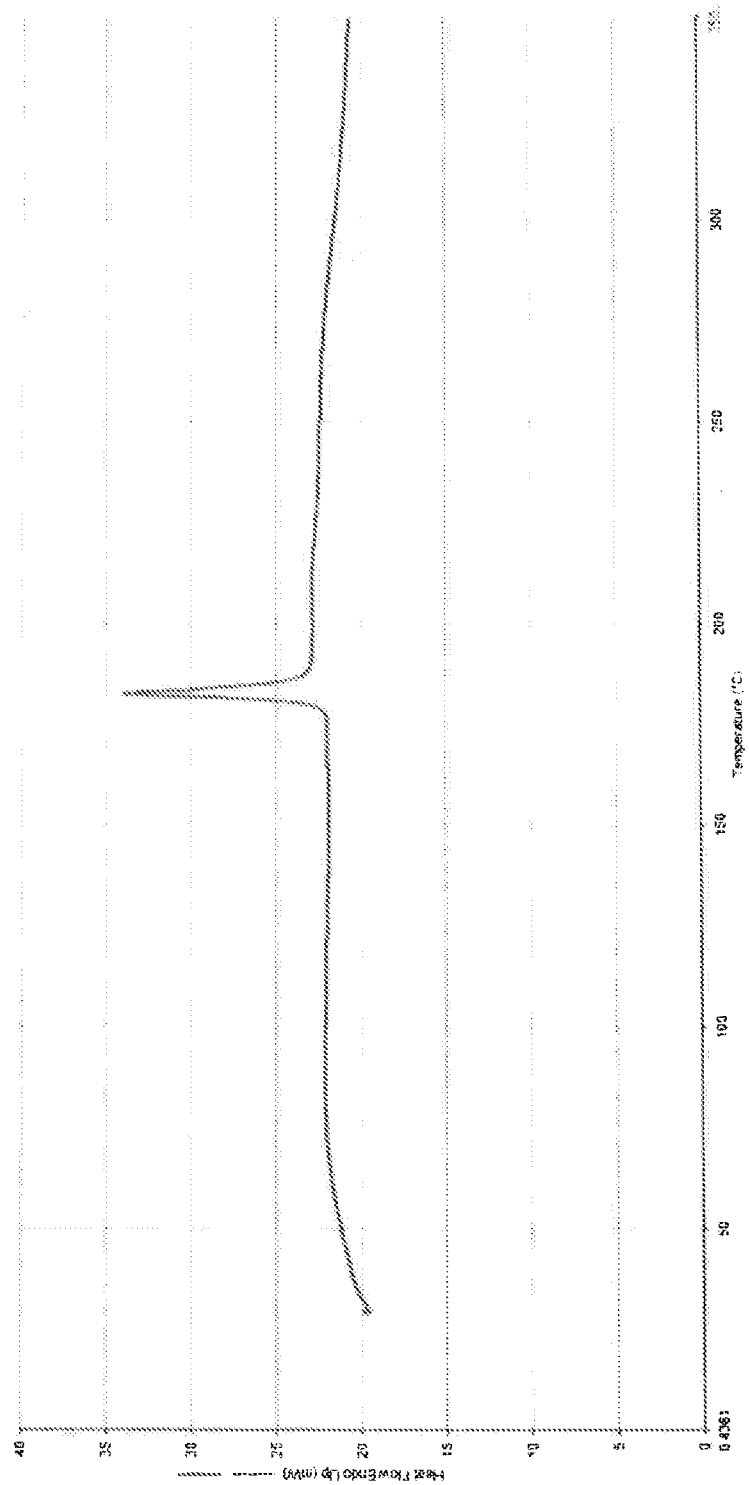
FIG. 29 shows a DSC trace for the 1:1 tranilast 2,4-dihydroxybenzoic acid cocrystal.

The differential scanning calorimetry (DSC) trace, FIG. 29, shows a sharp endotherm with a peak maximum of 182.5° C. corresponding to the melt of the cocrystal.

7.4 TGA of the 1:1 Tranilast 2,4-Dihydroxybenzoic Acid Cocrystal

Figure 30:
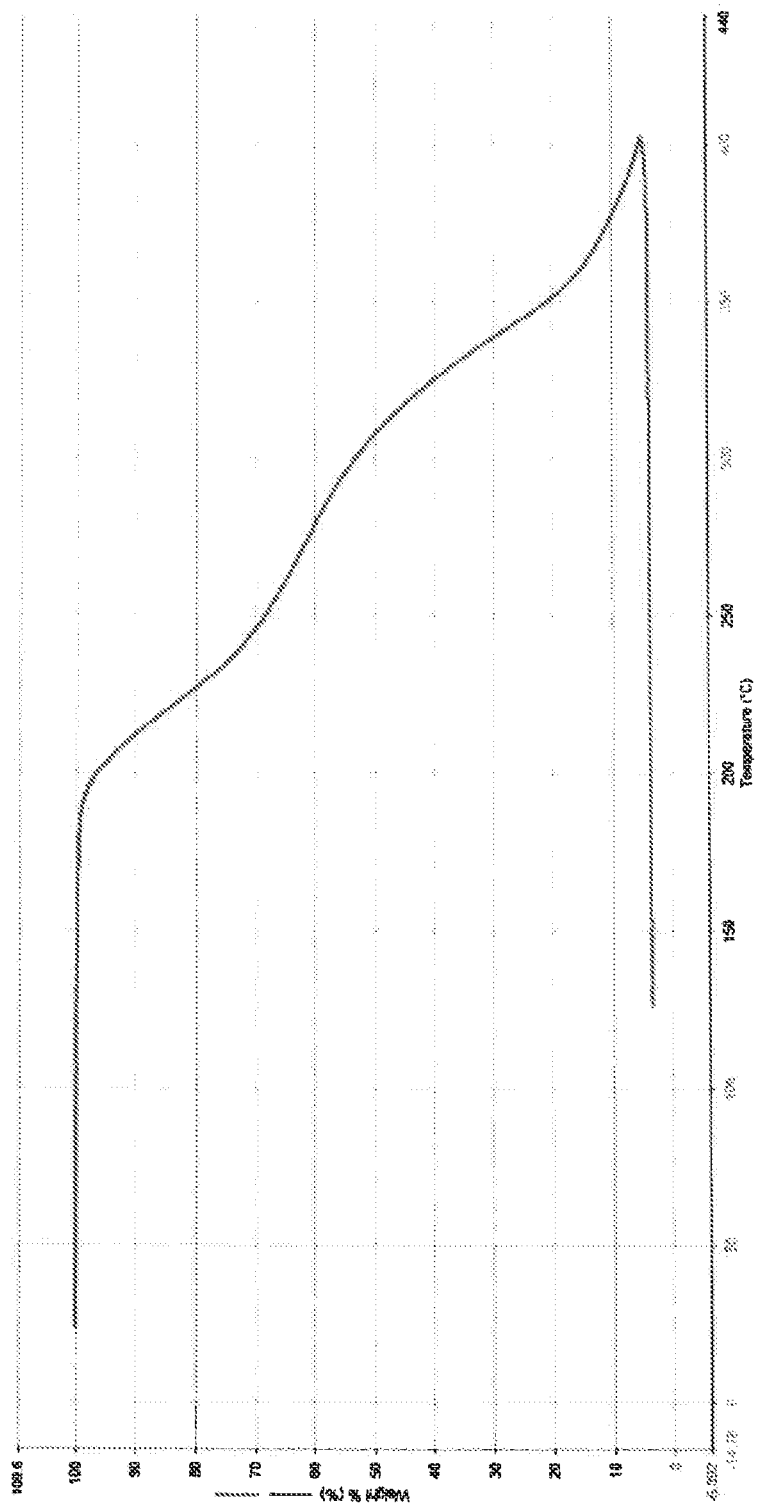
FIG. 30 shows a TGA trace for the 1:1 tranilast 2,4-dihydroxybenzoic acid cocrystal.

The thermal gravimetric analysis (TGA) trace, FIG. 30, shows no significant weight loss prior to the melt temperature of the cocrystal with 99.5% weight remaining at 180° C. The TGA shows that there is a weight loss of 32% between 182 and 251° C. This corresponds to one molar equivalent of 2,4-dihydroxybenzoic acid.

7.5 $^1$H NMR Spectrum of the 1:1 Tranilast 2,4-Dihydroxybenzoic Cocrystal

Figure 31:
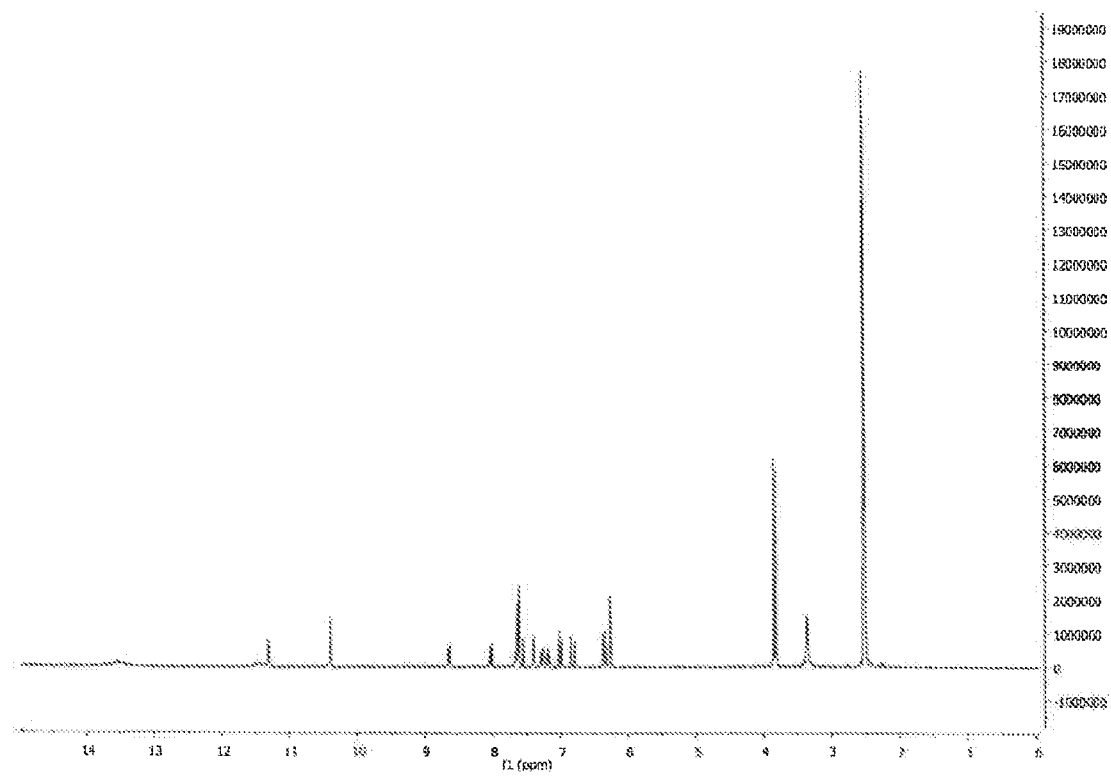
FIG. 31 shows the $^1$H NMR spectrum of 1:1 tranilast 2,4-dihydroxybenzoic acid cocrystal.

The $^1$H NMR spectrum of the 1:1 tranilast 2,4-dihydroxybenzoic acid cocrystal, shown in FIG. 31, displays the following peaks: $^1$H NMR (400 MHz, d6-DMSO) δ: 13.53 (1H), 11.43 (1H), 11.30 (1H), 10.39 (1H), 8.63 (1H), 8.02 (1H), 7.55-7.66 (3H), 7.40 (1H), 7.26 (1H), 7.18 (1H), 7.01 (1H), 6.81 (1H), 6.34 (1H), 6.27 (1H), 3.84 (3H) and 3.81 (3H). The peak at 6.27 ppm in the $^1$H NMR spectrum corresponds to one proton on the aromatic ring of 2,4-dihydroxybenzoic acid. Comparison of the integration of this peak with that at 8.63 ppm, which corresponds to one of the aromatic protons of tranilast, indicates that the cocrystal has an API:coformer stoichiometry of 1:1.

Example 8

Solid-State Photostability Study

It is known that while pure crystalline tranilast is photostable in the solid form, other solid forms of the API are not as photostable (S. Onoue. *Eur J Pharm Sci.* 2010; 39: 256-262). A study was, therefore, carried out to determine the solid-state photostability of the 1:1 tranilast nicotinamide cocrystal, the 1:1 tranilast saccharin cocrystal, the 1:1 tranilast gentisic acid cocrystal, the 1:1 salicylic acid cocrystal, the 1:1 tranilast urea cocrystal, the 1:1 tranilast 4-aminobenzoic acid cocrystal and the 1:1 tranilast 2,4-dihydroxybenzoic acid cocrystal and to compare this with the solid state photostability of pure crystalline tranilast. A 1-2 mg sample of crystalline tranilast and the seven cocrystal forms were each weighed and spread over the bottom surface of a clear glass vial. The vials were placed into a Vindon Scientific Photostability cabinet and irradiated with UV light (average Klux=18.2 (18.2 Lux/hour), average UV values=2.55 watts/minute, temperature=31.0-32.0° C.). The percentage of tranilast remaining in each sample, that had not undergone degradation into the cis-isomer, dimer or any other degradation product, was determined at 3, 24 and 48 hours using HPLC. The HPLC method used is described in Table 10.

TABLE 10

| | | | |
|---|---|---|---|
| Mobile Phase A | 0.1% formic acid in purified water | | |
| Mobile Phase B | 0.1% formic acid in methanol | | |
| Column | Zorbax Eclipse XDB-C18 50 × 4.6 mm, 1.8 μm PS | | |
| Column Temperature | 35° C. | | |
| Flow Rate | 1.0 ml/min | | |
| Injection Volume | 5 μl | | |
| Wavelength | 340 nm | | |
| Run time | 3 minutes | | |
| | Time (min) | % A | % B |
| Gradient Program | 0 | 80 | 20 |
| | 4 | 5 | 95 |
| | 8 | 5 | 95 |
| | 8.1 | 80 | 20 |

The results of this study are shown in Table 11. It can be seen from Table 11 that in the solid-state the cocrystals are all photostable under these conditions, with no indication of any photodegradation. The study suggests that the 1:1 tranilast nicotinamide cocrystal, the 1:1 tranilast saccharin cocrystal, the 1:1 tranilast gentisic acid cocrystal, the 1:1 salicylic acid cocrystal, the 1:1 tranilast urea cocrystal, the 1:1 tranilast 4-aminobenzoic acid cocrystal and the 1:1 tranilast 2,4-dihydroxybenzoic acid cocrystal all have comparable photostability in the solid-state to that of pure crystalline tranilast.

TABLE 11

| | Time | | |
|---|---|---|---|
| | 3 hrs | 24 hrs | 48 hrs |
| Crystalline Tranilast | 98.9% | 99.8% | 99.7% |
| 1:1 Tranilast Nicotinamide Cocrystal | 99.3% | 99.9% | 99.9% |
| 1:1 Tranilast 4-Aminobenzoic Acid Cocrystal | 99.8% | 98.2% | 99.7% |
| 1:1 Tranilast 2,4-Dihydroxybenzoic Acid Cocrystal | 99.9% | 99.7% | 99.8% |
| 1:1 Tranilast Gentisic Acid Cocrystal | 99.6% | 99.8% | 99.9% |
| 1:1 Tranilast Saccharin Cocrystal | 99.8% | 99.6% | 99.1% |
| 1:1 Tranilast Urea Cocrystal | 99.8% | 99.6% | 99.9% |
| 1:1 Tranilast Salicyclic Acid Cocrystal | 99.8% | 99.6% | 98.7% |

Example 9

Solution Photostability Study

Crystalline tranilast is photochemically unstable once dissolved in solution, transforming into cis-isomer and dimer forms upon UV exposure (N. Hori. *Chem Pharm Bull.* 1999; 47: 1713-1716). This study explored the photostability of the 1:1 tranilast nicotinamide cocrystal, the 1:1 tranilast saccharin cocrystal, the 1:1 tranilast gentisic acid cocrystal, the 1:1 salicylic acid cocrystal, the 1:1 tranilast urea cocrystal, the 1:1 tranilast 4-aminobenzoic acid cocrystal and the 1:1 tranilast 2,4-dihydroxybenzoic acid cocrystal once dissolved in solution and to compare these with the solution photostability of pure tranilast. A 1 mg sample of crystalline tranilast and the seven cocrystal forms were each weighed into a clear glass vial. Each sample was dissolved in a mixture of DMSO (200 µl), MeOH (600 µl) and water (600 µl). The vials were placed into a Vindon Scientific Photostability cabinet and irradiated with UV light (average Klux=18.2 (18.2 Lux/hour), average UV values=2.55 watts/minute, temperature=31.0-32.0° C.). The percentage of tranilast remaining in each sample, that had not undergone degradation into the cis-isomer, dimer or any other degradation product, was determined after 24 hours using HPLC. The HPLC method used is described in Table 10. The results of this study are shown in Table 12.

TABLE 12

| Composition | Time 24 hrs |
|---|---|
| Crystalline Tranilast | 66.2% |
| 1:1 Tranilast Nicotinamide Cocrystal | 80.2% |
| 1:1 Tranilast 4-Aminobenzoic Acid Cocrystal | 76.2% |
| 1:1 Tranilast 2,4-Dihydroxybenzoic Acid Cocrystal | 79.1% |
| 1:1 Tranilast Gentisic Acid Cocrystal | 76.3% |
| 1:1 Tranilast Saccharin Cocrystal | 71.0% |
| 1:1 Tranilast Urea Cocrystal | 76.4% |
| 1:1 Tranilast Salicyclic Acid Cocrystal | 77.5% |

It can be seen from Table 12 that the cocrystal forms of tranilast have higher photostability in solution after 24 hours compared with pure crystalline tranilast.

Example 10

Dissolution Study

Figure 32:
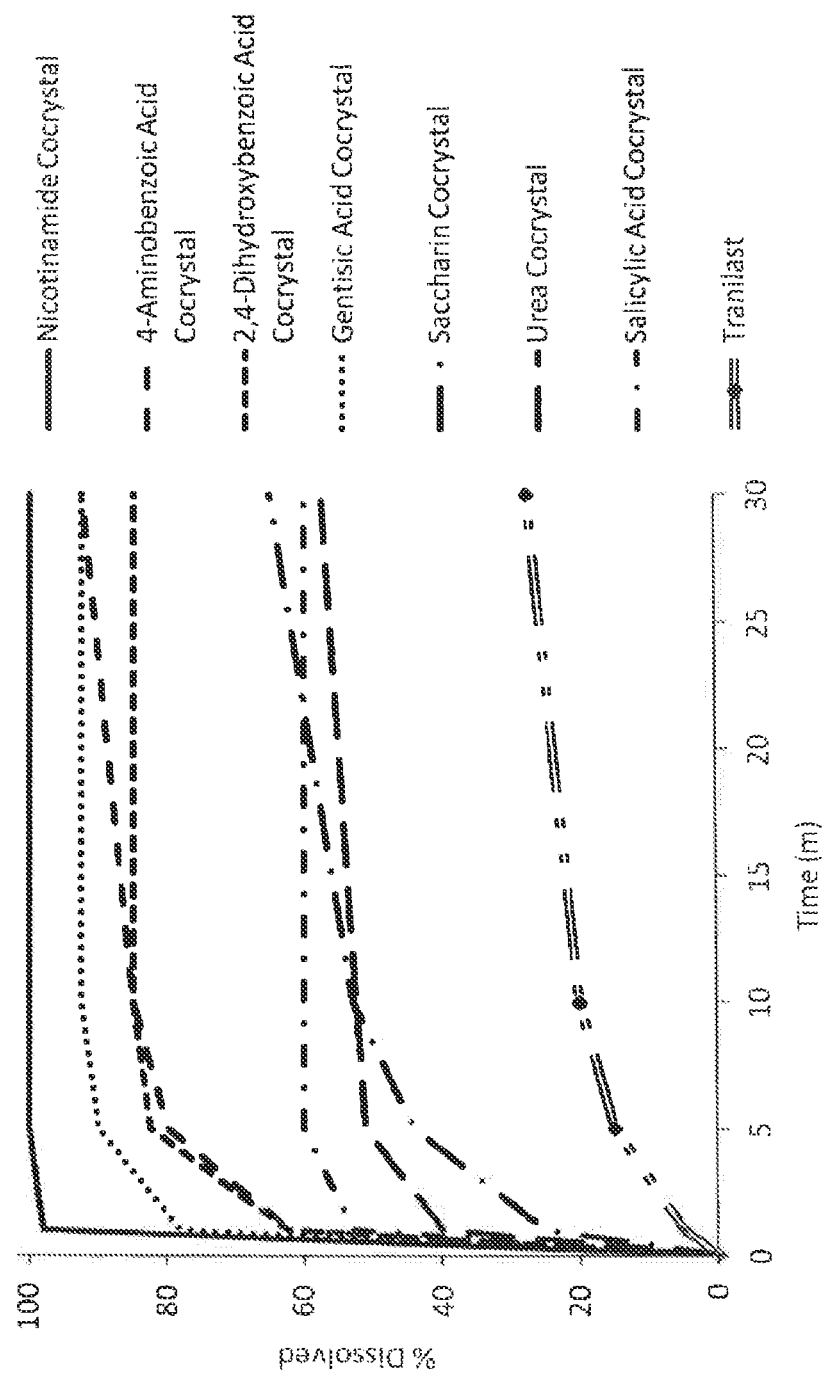
FIG. 32 shows the dissolution profiles, over 30 minutes, for crystalline tranilast and the tranilast cocrystals of the invention, in purified water containing 2% SDS.

For poorly soluble drugs, such as tranilast, the rate of dissolution of the drug form used can have an impact on the overall absorption and thus bioavailability of the drug, especially for example, in the case of oral solid dosage or inhalation delivery methods. A study was, therefore, carried out to examine the rate of dissolution of the 1:1 tranilast nicotinamide cocrystal, the 1:1 tranilast saccharin cocrystal, the 1:1 tranilast gentisic add cocrystal, the 1:1 salicylic acid cocrystal, the 1:1 tranilast urea cocrystal, the 1:1 tranilast 4-aminobenzoic acid cocrystal and the 1:1 tranilast 2,4-dihydroxybenzoic acid cocrystal compared with that of pure crystalline tranilast. The dissolution experiment was carried out for tranilast and each of the cocrystal forms at a concentration equivalent to 0.4 mg tranilast/ml in purified water containing 2% SDS. This study compared the dissolution rates of the cocrystals versus pure crystalline tranilast, because of the extremely low solubility of crystalline tranilast in aqueous media, the surfactant sodium dodecyl sulfate (SDS) was added to the dissolution media to allow easier analytical detection. Samples were collected and analyzed at 1, 5, 10 and 30 minute time points. The samples were analyzed by HPLC using the method described in Table 10. FIG. 32 illustrates the dissolution profiles from a single dataset for each of the tranilast cocrystals alongside crystalline tranilast over the 30 minute time period in the aqueous 2% SDS solution. The dissolution data is corrected within error limits of the analytical method described (estimated at ±10%). It can be seen from this graph that all of the cocrystals demonstrate accelerated dissolution behaviour in this media compared to crystalline tranilast. Most of the cocrystals reach almost their maximum dissolution within the first minute. In particular the 1:1 tranilast nicotinamide cocrystal shows almost complete dissolution within 1 minute whereas the crystalline tranilast is only about 5% dissolved after this time. It can be seen that all of the cocrystals have different dissolution rates in this media demonstrating how different cocrystals can impart different properties to tranilast and that the exact properties of a cocrystal can not be predicted simply from the properties of the coformer used.

The claimed invention is:

1. A 1:1 tranilast nicotinamide cocrystal, wherein the cocrystal is characterised by at least one of:
    a powder X-ray diffraction pattern having at least three peaks selected from 6.0, 8.0, 12.0, 15.0 and 15.6 °2θ±0.2°2θ; or
    a powder X-ray diffraction pattern substantially similar to FIG. 1.

2. A pharmaceutical composition comprising a tranilast cocrystal of claim 1 and a pharmaceutically acceptable carrier.

3. A pharmaceutical composition of claim 2, wherein the composition is a topical formulation.

4. A pharmaceutical composition of claim 2, wherein the composition is an inhalable formulation.

5. A method of preparing a liquid pharmaceutical composition comprising the step of dissolving a tranilast cocrystal of claim 1 in a pharmaceutically acceptable solvent.

6. A pharmaceutical composition of claim 2, wherein the composition is an oral formulation.

7. A pharmaceutical composition of a tranilast cocrystal of claim 1 prepared by dissolving the tranilast cocrystal in a pharmaceutically acceptable solvent.

8. A pharmaceutical composition of claim 7, wherein the pharmaceutical composition is an injectable formulation.

* * * * *